United States Patent
Kinzie et al.

(10) Patent No.: US 10,894,848 B2
(45) Date of Patent: *Jan. 19, 2021

(54) POLYARYLENE RESINS

(71) Applicant: Rohm and Haas Electronic Materials LLC, Marlborough, MA (US)

(72) Inventors: Charles R. Kinzie, Boston, MA (US); Daniel Greene, Shrewsbury, MA (US); Christopher Gilmore, Natick, MA (US); James F. Cameron, Brookline, MA (US); Ping Ding, Acton, MA (US); Qing Min Wang, North Andover, MA (US); Young-Seok Kim, Shrewsbury, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 96 days.

This patent is subject to a terminal disclaimer.

(21) Appl. No.: 15/790,606

(22) Filed: Oct. 23, 2017

(65) Prior Publication Data

US 2018/0162968 A1    Jun. 14, 2018

Related U.S. Application Data

(60) Provisional application No. 62/434,070, filed on Dec. 14, 2016.

(51) Int. Cl.

| | | |
|---|---|---|
| *C07C 49/537* | (2006.01) | |
| *C08F 32/06* | (2006.01) | |
| *C08L 45/00* | (2006.01) | |
| *C08G 61/10* | (2006.01) | |
| *C08G 61/12* | (2006.01) | |
| C08L 67/03 | (2006.01) | |
| H01L 23/532 | (2006.01) | |
| C09D 165/02 | (2006.01) | |
| C08L 65/02 | (2006.01) | |

(52) U.S. Cl.
CPC ............. *C08F 32/06* (2013.01); *C08G 61/10* (2013.01); *C08G 61/12* (2013.01); *C08L 45/00* (2013.01); *C07C 49/537* (2013.01); *C08G 2261/135* (2013.01); *C08G 2261/1426* (2013.01); *C08G 2261/312* (2013.01); *C08G 2261/46* (2013.01); *C08G 2261/64* (2013.01); *C08G 2261/65* (2013.01); *C08G 2261/76* (2013.01); *C08L 65/02* (2013.01); *C08L 67/03* (2013.01); *C09D 165/02* (2013.01); *H01L 23/5329* (2013.01)

(58) Field of Classification Search
CPC ........ C07C 49/537; C08L 65/02; C08L 45/00; C08L 67/03; C08F 32/06; C08G 61/10; C08G 61/12; C09D 165/02
See application file for complete search history.

(56) References Cited

U.S. PATENT DOCUMENTS

| | | | |
|---|---|---|---|
| 4,400,540 A | * | 8/1983 | Reinhardt ............... C07C 45/74 528/183 |
| 6,359,091 B1 | | 3/2002 | Godschalx et al. |
| 7,816,482 B1 | | 10/2010 | Hibbs et al. |
| 9,868,820 B2 | | 1/2018 | Gilmore et al. |
| 2002/0086429 A1 | | 7/2002 | Mohler et al. |
| 2004/0198850 A1 | | 10/2004 | Connor et al. |
| 2015/0038666 A1 | | 2/2015 | Miyazaki et al. |
| 2016/0289493 A1 | | 10/2016 | Kang et al. |

FOREIGN PATENT DOCUMENTS

| | | |
|---|---|---|
| JP | 2000191752 A | 7/2000 |
| JP | 2004292554 A | 10/2004 |
| JP | 2010027165 A | 2/2010 |
| JP | 2010271654 A | 2/2010 |

OTHER PUBLICATIONS

Skalski et al; JACS, 2015, 137 (12223-12226).*
Seok Jin Park et al, "Highly phenyl-substituted fluorene copolymers for light-emitting diode", Materials Science and Engineering, Jan. 5, 2004, pp. 99-102, vol. 24, No. 1-2.
Search report for corresponding Europe Application No. 17 20 5302 dated May 2, 2018.
Search report for corresponding Taiwan Application No. 106139624 dated Jul. 9, 2018.
Search report corresponding with China Application No. 201711160870.5 dated Mar. 15, 2020.

* cited by examiner

*Primary Examiner* — Karuna P Reddy
(74) *Attorney, Agent, or Firm* — Jonathan D. Baskin

(57) ABSTRACT

Certain cyclopentadienone monomers having polar moieties are useful in forming polyarylene resins having improved solubility in certain organic solvents and are useful in forming polyarylene resin layers in electronics applications.

10 Claims, No Drawings

POLYARYLENE RESINS

The present invention relates generally to the field of polyarylene materials and more particularly to polyarylene oligomers for use in electronics applications.

Polymer materials may be used as insulating layers, underlayers, or the like in the manufacture of various electronic devices, such as integrated circuits, multichip modules, laminated circuit boards, displays and the like. The electronics fabrication industry has different requirements for polymer materials, such as dielectric constant, coefficient of thermal expansion, modulus, etch selectivity, and the like, depending upon the particular application.

Various inorganic materials, such as silica, silicon nitride and alumina, have been used as dielectric materials in electronic devices. These inorganic materials generally can be deposited in thin layers, typically by vapor deposition techniques, and have advantageous properties, such as not readily absorbing water. Polymer dielectric materials often possess properties which offer advantages over inorganic dielectric materials in certain applications, such as ease of application such as by spin-coating techniques, gap-filling ability, lower dielectric constants, and the ability to withstand certain stresses without fracturing, that is, polymer dielectrics can be less brittle than inorganic dielectric materials. However, polymer dielectrics often present challenges to process integration during fabrication. For example, to replace silicon dioxide as a dielectric in certain applications such as integrated circuits, the polymer dielectric must be able to withstand processing temperatures during metallization and annealing steps of the process. In general, the polymer dielectric material should have a glass transition temperature greater than the processing temperature of subsequent manufacturing steps. Also, the polymer dielectric should not absorb water which may cause an increase in the dielectric constant and potential corrosion of metal conductors.

Polyarylene polymers are well-known as dielectric materials and possess many desirable properties. For example, International Pat. App. No. WO 97/10193 discloses certain polyarylene oligomers prepared from certain ethynyl-substituted aromatic compounds and a biscyclopentadienone monomer. The aromatic ring in these ethynyl-substituted aromatic compounds may be substituted with certain substituents such as $CF_3$—, $CF_3O$—, ArO—, ArS—, or $(Ar)_2P$ (=O)—, wherein Ar designates a certain aromatic ring. Polyarylene oligomers are prepared at relatively high temperatures in organic solvents having relatively high boiling points (typically ≥150° C.). However, such reaction solvents are poor choices as casting solvents in the electronics industry, and the polyarylene oligomers must be precipitated from the reaction solvent and taken up in a different organic solvent with a much lower boiling point that is suitable for casting films of these polymers. Such polyarylene oligomers suffer from limited solubility in organic solvents conventionally used in the electronics industry, limiting the use of these polymers. U.S. Published Pat. App. No. 2016/0060393 discloses polar moiety-terminated polyarylene oligomers having improved solubility prepared by reacting a first monomer comprising two cyclopentadienone moieties, an ethynyl-substituted aromatic compound as a second monomer, and as a third monomer a monoethynyl-substituted compound of the formula

wherein $R^2$ is H, optionally substituted $C_{1-10}$ alkyl, optionally substituted $C_{7-12}$ aralkyl, optionally substituted $C_{6-10}$ aryl, or $R^3$, and $R^3$ is a polar moiety. While these polar moiety-terminated polyarylene oligomers do have improved solubility in certain organic solvents as compared to conventional polyarylene oligomers, the solubility improvement in some solvents is not sufficient to allow these polyarylene oligomers to be used in certain applications in the electronics industry. There remains a need in the industry for polyarylene polymers having improved solubility in organic solvents, particularly in organic solvents used to cast polymer films in the electronics industry.

Harris et al., *Polym. Prepr., Am. Chem. Soc., Div. Polym. Chem.*, 19(2), 394 (1978), disclose polyphenylenes prepared by polymerizing the compound of the formula (I)

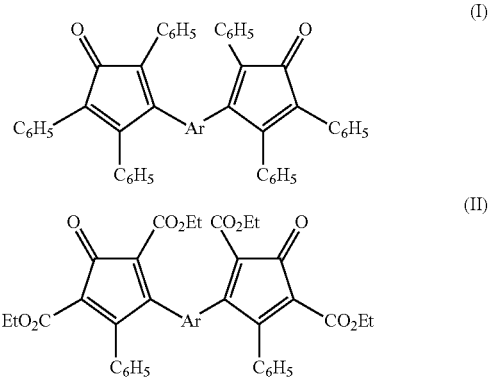

wherein

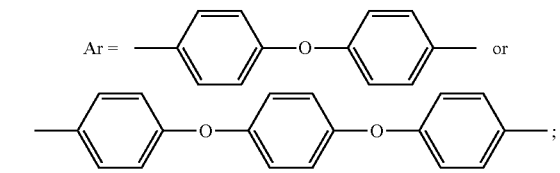

a compound of formula (II) wherein

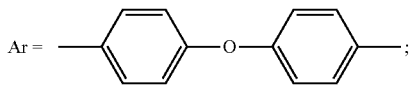

and 1,4-diethynylbenzene (III). The ratio of (I) to (II) to (III) was 80:20:100 or 95:5:100. These polyphenylene polymers show a weight loss upon heating between 365 and 550° C. that closely corresponds to the weight of the ethoxycarbonyl substituent in the polymer. This reference indicates that after such initial weight loss, the TGA (thermal gravimetric analysis) curves of these polymers closely resemble the TGA curves of phenylated polyphenylenes, that is, polyphenylenes that do not contain ethoxycarbonyl substituents on the cyclopentadienone ring. In other words, heating these polymers to temperatures between 365 and 550° C. essentially removes the ethoxycarbonyl substituent from the polymers. The weight loss shown by the polymers of Harris et al. indicate such polymers lack adequate thermal stability for many applications, such as where outgassing, film shrinkage, and the like must be minimized. Accordingly, there remains a need for polyphenylene polymers having good solubility in various solvents and good thermal stability.

The present invention provides a monomer of the formula (1)

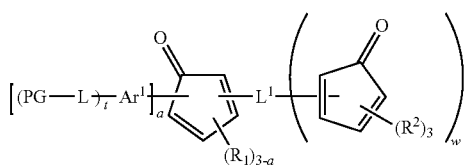

(1)

wherein each $R^1$ is independently chosen from H, $C_{1-20}$-alkyl, and optionally substituted $C_{5-30}$-aryl; each $R^2$ is independently chosen from H, $C_{1-20}$-alkyl, optionally substituted $C_{5-30}$-aryl, and $(PG\text{-}L)_t\text{-}Ar^1$—; PG is a polar moiety; each $Ar^1$ is independently optionally substituted $C_{5-30}$-aryl; each of L and $L^1$ is independently a linking group or a single chemical bond; L and $L^1$ may be the same as or different; a is an integer from 0 to 3; t is an integer from 1 to 4; and w is an integer from 1 to 4; provided that when a=0, $L^1$ has the formula (1a)

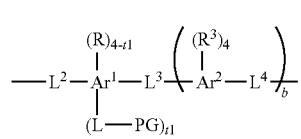

(1a)

wherein $Ar^2$ is a $C_{5-30}$-aryl; each $R^3$ is independently chosen from H, $C_{1-20}$-alkyl, optionally substituted $C_{5-30}$-aryl, and $(PG\text{-}L)_t\text{-}Ar^1$—; each of $L^2$, $L^3$ and $L^4$ is independently a single chemical bond or a divalent linking group; t is an integer from 1 to 4; t1 is an integer from 1 to 4; b is 0 or 1; and $L^2$, $L^3$ and $L^4$ may be the same or different. When a=0, it is preferred that L is a divalent linking group.

Also provided by the present invention is a polyarylene resin comprising as polymerized units one or more first cyclopentadienone monomers of formula (1) described above, and one or more polyalkynyl-substituted second monomers. The present invention further provides a polyarylene resin composition comprising the polyarylene resin described above and one or more organic solvents.

Still further, the present invention provides a method of manufacturing an electronic device comprising providing a substrate; coating a layer of the polyarylene resin composition described above on a surface of the substrate; removing any organic solvent; and curing the polyarylene resin to form a dielectric material layer.

The present invention even further provides a method of forming a patterned layer comprising: (a) coating on an electronic device substrate a layer of a polyarylene resin composition; (b) removing organic solvent to form an polyarylene resin layer; (c) coating a layer of a photoresist on the polyarylene resin layer; (d) exposing the photoresist layer to actinic radiation through a mask; (e) developing the exposed photoresist layer to form a resist pattern; and (f) transferring the pattern to the polyarylene resin layer to expose portions of the substrate; wherein the polyarylene resin composition comprises (A) one or more polyarylene resins comprising as polymerized units (i) one or more first monomers of formula (1)

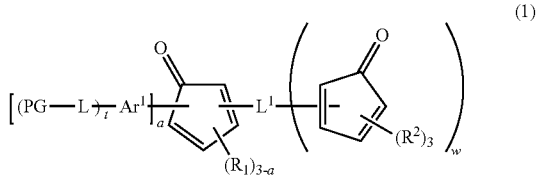

(1)

wherein each $R^1$ is independently chosen from H, $C_{1-20}$-alkyl, and optionally substituted $C_{5-30}$-aryl; each $R^2$ is independently chosen from H, $C_{1-20}$-alkyl, optionally substituted $C_{5-30}$-aryl, and $(PG\text{-}L)_t\text{-}Ar^1$—; PG is a polar moiety; each $Ar^1$ is independently optionally substituted $C_{5-30}$-aryl; each of L and $L^1$ is independently a linking group or a single chemical bond; L and $L^1$ may be the same as or different; a is an integer from 0 to 3; t is an integer from 1 to 4; and w is an integer from 1 to 4; provided that when a=0, $L^1$ has the formula (1a)

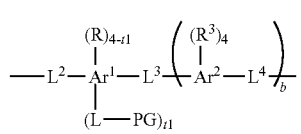

(1a)

wherein $Ar^2$ is a $C_{5-30}$-aryl; each $R^3$ is independently chosen from H, $C_{1-20}$-alkyl, optionally substituted $C_{5-30}$-aryl, and $(PG\text{-}L)_t\text{-}Ar^1$—; each of $L^2$, $L^3$ and $L^4$ is independently a single chemical bond or a divalent linking group; t is an integer from 1 to 4; t1 is an integer from 1 to 4; b is 0 or 1; $L^2$, $L^3$ and $L^4$ may be the same or different; and (ii) one or more polyalkynyl-substituted second monomers; and (B) one or more organic solvents.

It will be understood that when an element is referred to as being "on" another element, it can be directly adjacent to the other element or intervening elements may be present therebetween. In contrast, when an element is referred to as being "directly on" another element, there are no intervening elements present. As used herein, the term "and/or" includes any and all combinations of one or more of the associated listed items.

It will also be understood that although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

As used throughout this specification, the following abbreviations shall have the following meanings, unless the context clearly indicates otherwise: ° C.=degree Celsius; g=gram; mg=milligram; L=liter; mL=milliliter; Å=angstrom; nm=nanometer; μm=micron=micrometer; mm=millimeter; sec.=second; min=minute; hr.=hour; DI=deionized; ca.=approximately; and Da=daltons. Unless otherwise specified, "wt %" refers to percent by weight based on the total weight of a referenced composition. All amounts are wt % and all ratios are molar ratios, unless otherwise specified. All numerical ranges are inclusive and combinable in any order, except where it is clear that such numerical ranges are constrained to add up to 100%. The articles "a", "an" and "the" refer to the singular and the plural. "Alkyl" refers to linear, branched and cyclic alkyl unless otherwise specified. "Alkyl" refers to an alkane radical, and includes alkane monoradicals, diradicals (alkylene), and higher-radicals. "Halo" refers to fluoro, chloro, bromo, and iodo. Unless otherwise noted, "alkyl" includes "heteroalkyl". The term "heteroalkyl" refers to an alkyl group with one or more heteroatoms, such as nitrogen, oxygen, sulfur, phosphorus, replacing one or more carbon atoms within the radical, for example, as in an ether or a thioether. In one preferred embodiment, "alkyl" does not include "heteroalkyl". If no number of carbons is indicated for any alkyl or heteroalkyl, then 1-12 carbons are contemplated.

The terms "aromatic moiety" and "aryl" are used interchangeably. "Aryl" includes aromatic carbocycles and aromatic heterocycles. The term "aryl" refers to an aromatic radical, and includes monoradicals, diradicals (arylene), and higher-radicals. It is preferred that aryl moieties are aromatic carbocycles. As used herein, an "optionally substituted" moiety refers to both an unsubstituted moiety and a substituted moiety, such as "optionally substituted aryl" refers to both unsubstituted aryl (or simply "aryl") and substituted aryl. "Substituted aryl" refers to any aryl moiety having one or more of its hydrogens replaced with one or more substituents chosen from halogen, $C_{1-6}$-alkyl, $C_{1-6}$-haloalkyl, phenyl, halophenyl, and phenoxy, preferably from halogen, $C_{1-6}$-alkyl, $C_{1-4}$-haloalkyl, phenyl, and phenoxy, and more preferably from halogen, $C_{1-6}$-alkyl, phenyl, and phenoxy. Preferably, a substituted aryl has from 1 to 3 substituents, and more preferably 1 or 2 substituents. "Substituted alkyl" refers to any alkyl moiety having one or more of its hydrogens replaced with one or more substituents chosen from halogen, oxygen and sulfur. Exemplary substituted alkyls include ketoalkyl, thioketoalkyl, and iminoalkyl. As used herein, the term "polymer" includes oligomers. The term "oligomer" refers to dimers, trimers, tetramers and other polymeric materials that are capable of further curing. By the term "curing" is meant any process, such as polymerization or condensation, that increases the overall molecular weight of the present resins, removes solubility enhancing groups from the present oligomers, or both increases the overall molecular weight and removes solubility enhancing groups. "Curable" refers to any material capable of being cured under certain conditions. As used herein, "gap" refers to any aperture on a semiconductor substrate that is intended to be filled with a polymer composition. When any linking group described herein is a single chemical bond, such chemical bond is a covalent bond.

Cyclopentadienone monomers of the present invention have 2 or more cyclopentadienone moieties, wherein at least one cyclopentadienone moiety is substituted with an aryl moiety having one or more polar moieties. Preferably, the present cyclopentadienone monomers have from 2 to 4 cyclopentadienone moieties, more preferably 2 or 3, and even more preferably 2 cyclopentadienone moieties. Suitable cyclopentadienone monomers are those of formula (1)

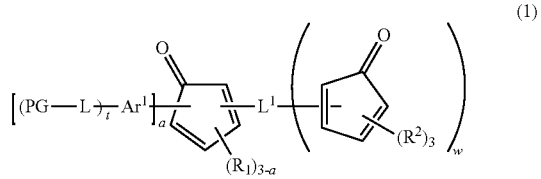

(1)

wherein each $R^1$ is independently chosen from H, $C_{1-20}$-alkyl, optionally substituted $C_{5-30}$-aryl; each $R^2$ is independently chosen from H, $C_{1-20}$-alkyl, optionally substituted $C_{5-30}$-aryl, and $(PG-L)_t-Ar^1-$; PG is a polar moiety; each $Ar^1$ is independently optionally substituted $C_{5-30}$-aryl; each of L and $L^1$ is independently a linking group or a single chemical bond; L and $L^1$ may be the same as or different; a is an integer from 0 to 3; t is an integer from 1 to 4; and w is an integer from 1 to 4; provided that when a=0, $L^1$ has the formula (1a)

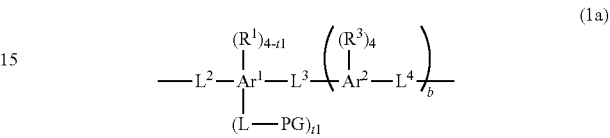

(1a)

wherein $Ar^2$ is a $C_{5-30}$-aryl; each $R^3$ is independently chosen from H, $C_{1-20}$-alkyl, optionally substituted $C_{5-30}$-aryl, and $(PG-L)_t-Ar^1-$; each of $L^2$, $L^3$ and $L^4$ is independently a single chemical bond or a divalent linking group; t is described above; t1 is an integer from 1 to 4; b is 0 or 1; and $L^2$, $L^3$ and $L^4$ may be the same or different. Preferably, a=0, 1 or 2, and more preferably a=0 or 1. It is preferred that each t is independently an integer from 1 to 3, more preferably each t=1 or 2, and even more preferably each t=1. It is preferred that w=1, 2 or 3, more preferably w=1 or 2, and yet more preferably w=1. Preferably, t1=1, 2 or 3, more preferably 1 or 2, and yet more preferably t1=1. Each $R^1$ is preferably independently chosen from optionally substituted $C_{5-30}$-aryl, and more preferably from $C_{5-30}$-aryl. Each $R^2$ is preferably independently chosen from optionally substituted $C_{5-30}$-aryl and $(PG-L^1)_t-Ar^1-$, and more preferably from $C_{5-30}$-aryl, and $(PG-L^1)_t-Ar^1-$. It is preferred that each $R^3$ is independently chosen from H, optionally substituted $C_{5-30}$-aryl, and $(PG-L)_t-Ar^1-$, and more preferably from H, $C_{5-30}$-aryl, and $(PG-L)_t-Ar^1-$. Preferably, each $Ar^1$ is independently optionally substituted $C_{6-30}$-aryl, more preferably optionally substituted $C_{6-20}$-aryl, and yet more preferably from $C_{6-20}$-aryl. $Ar^2$ is preferably optionally substituted $C_{6-30}$-aryl, and more preferably $C_{6-20}$-aryl. Preferably, L and $L^1$ are different. In one preferred embodiment, $L^2$ and $L^4$ are the same. In another preferred embodiment, $L^2$, $L^3$ and $L^4$ are the same. In a further preferred embodiment, $L^3$ is a chemical bond. When a=0, it is further preferred that each $R^2$ is independently chosen from H, $C_{1-20}$-alkyl, and optionally substituted $C_{5-30}$-aryl, and more preferably from H and optionally substituted $C_{5-30}$-aryl.

L in formula (1) is a single chemical bond or any divalent linking group suitable for linking polar moiety PG to $Ar^1$. It is preferred that L is a single chemical bond or an organic radical having 1 to 40 carbon atoms, and more preferably a single chemical bond or an organic radical having 1 to 30 carbon atoms. The organic radical of L may optionally contain one or more heteroatoms chosen from O, S, N, and combinations thereof, and preferably contains from 0 to 10 heteroatoms, and more preferably from 0 to 8 heteroatoms. Preferably, each L is chosen from single chemical bond, —O—, —S—, —S(=O)—, —S(=O)$_2$—, optionally substituted $C_{5-30}$-aryl, optionally substituted $C_{5-30}$-aryl-O-optionally substituted $C_{5-30}$-aryl, optionally substituted $C_{5-30}$-aryl-optionally substituted $C_{5-30}$-aryl, optionally substituted $C_{1-30}$-alkyl such as $C_{1-30}$-ketoalkyl, optionally substituted $C_{1-10}$-alkyl-optionally substituted $C_{5-30}$-aryl such as $C_{1-10}$-ketoalkyl-$C_{5-30}$-aryl, and the like. More preferably, each L is independently a single chemical bond, —O—, —S—, —S(=O)—, —S(=O)$_2$—, —C(=O)—C$_6$H$_4$—, —C(=O)—C$_{10}$H$_6$—, —C(=O)—C$_{16}$H$_8$—, —CH$_2$—C$_6$H$_4$—, —CH$_2$—C$_{10}$H$_6$—, —CH$_2$—C$_6$H$_4$—, —C$_2$H$_4$—C$_6$H$_4$—, —C$_6$H$_4$—, —C$_6$H$_4$—C$_6$H$_4$—, —C$_6$H$_4$—O—, —C$_6$H$_4$—O—C$_6$H$_4$—, —C$_{10}$H$_6$—, —C$_{16}$H$_8$—, C$_{1-10}$-alkyl, C$_{1-10}$-ketoalkyl, C$_{1-10}$-heteroalkyl, —C(C$_6$H$_5$)H—, —C(C$_{10}$H$_9$)H—, —C(C$_6$H$_5$)$_2$—, and the like, even more preferably a single chemical bond, —O—, —C(=O)—, —CH$_2$C(=O)—, —CH$_2$C(=O)CH$_2$—, —C(=O)—C$_6$H$_4$—, —C(=O)—C$_{10}$H$_6$—, —C(=O)—C$_{16}$H$_8$—, —CH$_2$—C$_6$H$_4$—, —CH$_2$—C$_{10}$H$_6$—, —CH$_2$—C$_6$H$_4$—, —CH$_2$—C$_6$H$_4$—CH$_2$—, —C$_2$H$_4$—C$_6$H$_4$—, —C$_6$H$_4$—, —C$_6$H$_4$—C$_6$H$_4$—, —C$_6$H$_4$—O—, —C$_6$H$_4$—O—C$_6$H$_4$—, —C$_{10}$H$_6$—, C$_{1-10}$-alkyl, C$_{1-10}$-heteroalkyl, —C(C$_6$H$_5$)H—, and —C(C$_6$H$_5$)$_2$—, and yet more preferably L is a single chemical bond.

The polar moieties of PG in formulas (1) and (1a) are any heteroatom-containing organic residue having from 0 to 30 carbons and one or more heteroatoms chosen from O, S and N, excluding alkoxy. Exemplary polar moieties include, without limitation, —OR$^4$, C$_{1-10}$-hydroxyalkyl, —C(=O)OR$^5$, —C(=O)N(R$^6$)$_2$, —O—C(=O)R$^7$, —NR$^6$C(=O)R$^8$, —N(R$^6$)$_2$, —N(R$^6$)$_3$$^+$An$^-$, —NO$_2$; —S(=O)$_2$—OR$^9$, —O—S(=O)$_2$—R$^{10}$, —NR$^6$—S(=O)$_2$—R$^8$, and —S(=O)$_2$—N(R$^6$)$_2$. Preferably, PG is chosen from —OR$^4$, C$_{1-4}$-hydroxyalkyl, —C(=O)OR$^5$, —C(=O)N(R$^6$)$_2$, —O—C(=O)R$^7$, —S(=O)$_2$—OR$^8$, and S(=O)$_2$—N(R$^6$)$_2$, more preferably from —OR$^4$, C$_{1-4}$-hydroxyalkyl, —C(=O)OR$^5$ and —C(=O)N(R$^6$)$_2$, and yet more preferably from —OH and —C(=O)OR$^5$. Each R$^4$ is independently H, C$_{1-10}$-hydroxyalkyl, C$_{1-10}$-aminoalkyl, C$_{5-30}$-aryl, or M, preferably H, C$_{1-10}$-hydroxyalkyl, C$_{1-10}$-aminoalkyl, or M, and more preferably H, C$_{1-10}$-hydroxyalkyl, or M. Most preferably, R$^4$=H. Each R$^5$ is independently H, C$_{1-10}$-alkyl, C$_{1-10}$-hydroxyalkyl, C$_{1-10}$-aminoalkyl, C$_{5-30}$-aryl, or M, and preferably H, C$_{1-10}$-hydroxyalkyl, or M. Most preferably, R$^5$=H. Each R$^6$ is independently chosen from H, C$_{5-30}$-aryl, and C$_{1-10}$-alkyl, and preferably from H and C$_{1-10}$-alkyl. Each R$^7$ is independently chosen from H, C$_{1-10}$-alkyl, C$_{1-10}$-hydroxyalkyl, C$_{5-30}$-aryl, —O(C$_{1-10}$-alkyl), —O(C$_{5-10}$-aryl), and —N(R$^6$)$_2$, and preferably from H, C$_{1-10}$-hydroxyalkyl, C$_{5-30}$-aryl, —O(C$_{1-10}$-alkyl), —O(C$_{5-10}$-aryl), and —N(R$^6$)$_2$. R$^8$=H, C$_{1-10}$-alkyl, C$_{1-10}$-hydroxyalkyl, C$_{5-30}$-aryl, —O(C$_{1-10}$-alkyl), or —NH(C$_{1-10}$-alkyl), and preferably R$^8$=H, C$_{1-10}$-hydroxyalkyl, C$_{5-30}$-aryl, or —NH(C$_{1-10}$-alkyl). R$^9$=H, C$_{1-10}$-alkyl, C$_{5-30}$-aryl, or M. R$^{10}$=C$_{5-30}$-aryl, C$_{1-10}$-alkyl, or C$_{1-10}$-haloalkyl, and preferably C$_{5-30}$-aryl, or C$_{1-10}$-alkyl. M=an alkali metal ion, an alkaline earth metal ion, or an ammonium ion, preferably an alkali metal ion or an ammonium ion, and more preferably an ammonium ion. An$^-$ is an anion chosen from halide and C$_{1-20}$-carboxylate.

In formula (1), when L$^1$ is a linking group, it may be any suitable group linking at least 2 cyclopentadienone moieties. It is preferred that L$^1$ is a single chemical bond or an organic radical having 1 to 60 carbon atoms, and more preferably a single chemical bond or an organic radical having 1 to 40 carbon atoms. The organic radical of L$^1$ may optionally contain one or more heteroatoms chosen from O, S, N, and combinations thereof, and preferably contains from 0 to 10 heteroatoms, and more preferably from 0 to 8 heteroatoms. Preferred heteroatoms for L$^1$ are O and N. The organic radical of L$^1$ may be aliphatic, aromatic, or a combination of aliphatic and aromatic. When w=1, L$^1$ is preferably a single chemical bond or a divalent linking group. Suitable linking groups for L$^1$ include, but are not limited to: optionally substituted C$_{1-40}$-alkyl, optionally substituted C$_{5-30}$-aryl, optionally substituted C$_{5-30}$-aryl-O-optionally substituted C$_{5-30}$-aryl, optionally substituted C$_{5-30}$-aryl-C$_{1-30}$-alkyl-optionally substituted C$_{5-30}$-aryl, optionally substituted C$_{5-30}$-aryl-optionally substituted C$_{5-30}$-aryl, combinations of any of the foregoing, and linking groups of formula (1a)

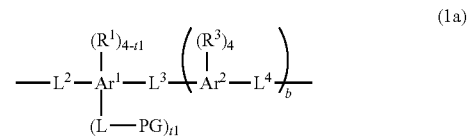

(1a)

wherein L, PG, L$^2$, L$^3$, L$^4$, Ar$^1$, Ar$^2$, R$^1$, R$^3$, t1, and b are as defined above. Exemplary linking groups for L$^1$ include, without limitation; —O—, —C$_{1-30}$-alkyl-, —C$_{1-30}$-ketoalkyl-, C$_{1-30}$-ketoalkyl-C$_{6-30}$-aryl, C$_{6-30}$-aryl, C$_{6-30}$-aryl-O—C$_{6-30}$-aryl, and C$_{6-30}$-aryl-O—C$_{6-30}$-aryl-O—C$_{6-30}$-aryl, and linking groups of formula (1a). Preferred linking groups for L$^1$ are —O—, —C$_{1-30}$-ketoalkyl-, —C$_{1-30}$-ketoalkyl-C$_{6-30}$-aryl, —C$_6$H$_4$—, —C$_{10}$H$_6$—, —C$_6$H$_4$—C$_6$H$_4$—, —C$_6$H$_4$—O—C$_6$H$_4$—, —C$_6$H$_4$—O—C$_6$H$_4$—O—C$_6$H$_4$—, and linking groups of formula (1a). It is preferred that L$^1$ is chosen from a single chemical bond, C$_{1-30}$-alkyl, C$_{1-30}$-ketoalkyl, C$_{6-30}$-aryl, substituted C$_{6-30}$-aryl, C$_{1-30}$-ketoalkyl-C$_{6-30}$-aryl, C$_{6-30}$-aryl-O—C$_{6-30}$-aryl, C$_{6-30}$-aryl-O—C$_{6-30}$-aryl-O—C$_{6-30}$-aryl, combinations of any of the foregoing, and linking groups of formula (1a), and more preferably from a single chemical bond, C$_{1-20}$-ketoalkyl, C$_{6-30}$-aryl, C$_{1-20}$-ketoalkyl-C$_{6-30}$-aryl, C$_{6-30}$-aryl-O—C$_{6-30}$-aryl, C$_{6-30}$-aryl-O—C$_{6-30}$-aryl-O—C$_{6-30}$-aryl, combinations of any of the foregoing, and linking groups of formula (1a).

In one preferred embodiment, L$^1$ has the formula (1a)

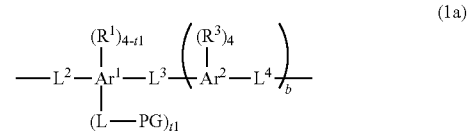

(1a)

wherein each R$^1$ is independently chosen from H, C$_{1-20}$-alkyl, optionally substituted C$_{5-30}$-aryl; PG is a polar moiety; Ar$^1$ is optionally substituted C$_{5-30}$-aryl; each of L, L$^2$, L$^3$, and L$^4$ is independently a linking group or a single chemical bond; Ar$^2$ is C$_{5-30}$-aryl; each R$^3$ is independently chosen from H, C$_{1-20}$-alkyl, optionally substituted C$_{5-30}$-aryl, and (PG-L)$_t$-Ar$^1$—; t is an integer from 1 to 4; t1 is an integer from 1 to 4; b is 0 or 1; and L, L$^2$, L$^3$ and L$^4$ may be the same or different. Preferably, t1=1, 2 or 3, more preferably 1 or 2, and yet more preferably t1=1. Each R$^1$ is preferably independently chosen from optionally substituted C$_{5-30}$-aryl, and more preferably from C$_{5-30}$-aryl. It is preferred that each R$^3$ is independently chosen from H, optionally substituted C$_{5-30}$-aryl, and (PG-L)$_t$-Ar$^1$—, and more preferably from H, C$_{5-30}$-aryl, and (PG-L)$_t$-Ar$^1$—. Preferably, each Ar$^1$ is independently optionally substituted C$_{6-30}$-aryl, more preferably optionally substituted C$_{6-20}$-aryl, and yet more preferably from C$_{6-20}$-aryl. Ar$^2$ is preferably optionally substituted C$_{6-30}$-aryl, and more preferably C$_{6-20}$-aryl. In one preferred embodiment, L$^2$ and L$^4$ are the same. In another preferred embodiment, L$^2$, L$^3$ and L$^4$ are the same. In a further preferred embodiment, L$^3$ is a chemical bond.

In formula (1a), any suitable divalent linking group may be used as the linking group for each of $L^2$, $L^3$ and $L^4$. Suitable linking groups are any organic radical having 1 to 60 carbon atoms, more preferably having 1 to 40 carbon atoms, and yet more preferably having 1 to 30 carbon atoms. The organic radical of $L^2$, $L^3$, or $L^4$ may optionally contain one or more heteroatoms chosen from O, S, N, and combinations thereof, and preferably contains from 0 to 10 heteroatoms, and more preferably from 0 to 8 heteroatoms. Preferred heteroatoms for use in any of $L^2$, $L^3$, and $L^4$ are O and N. The organic radical of any of $L^2$, $L^3$, and $L^4$ may be aliphatic, aromatic, or a combination of aliphatic and aromatic. It is preferred that each of $L^2$, $L^3$, and $L^4$ is chosen from a single chemical bond or an organic radical having 1 to 60 carbon atoms, and more preferably a single chemical bond or an organic radical having 1 to 40 carbon atoms. Suitable linking groups for $L^2$, $L^3$, and $L^4$ include, but are not limited to: optionally substituted $C_{1-40}$-alkyl, optionally substituted $C_{5-30}$-aryl, optionally substituted $C_{5-30}$-aryl-O-optionally substituted $C_{5-30}$-aryl, optionally substituted $C_{5-30}$-aryl-$C_{1-30}$-alkyl-optionally substituted $C_{5-30}$-aryl, optionally substituted $C_{5-30}$-aryl-optionally substituted $C_{5-30}$-aryl, and combinations of any of the foregoing. Exemplary linking groups for each of $L^2$, $L^3$, and $L^4$ include, without limitation; —O—, —$C_{1-30}$-alkyl-, —$C_{1-30}$-ketoalkyl-, —$C_{1-30}$-ketoalkyl-$C_{6-30}$-aryl-, —$C_{6-30}$-aryl-, —$C_{6-30}$-aryl-O—$C_{6-30}$-aryl-, and —$C_{6-30}$-aryl-O—$C_{6-30}$-aryl-O—$C_{6-30}$-aryl-. It is preferred that each of $L^2$, $L^3$, and $L^4$ is chosen from a single chemical bond, —O—, —$C_{1-30}$-alkyl-, —$C_{1-30}$-ketoalkyl-, —$C_{1-30}$-ketoalkyl-$C_{6-30}$-aryl-, —$C_{6-30}$-aryl-, —$C_{6-30}$-aryl-O—$C_{6-30}$-aryl-, —$C_{6-30}$-aryl-O—$C_{6-30}$-aryl-O—$C_{6-30}$-aryl-, and combinations of the foregoing. More preferably, each of $L^2$, $L^3$, and $L^4$ is chosen from a single chemical bond, —O—, —$C_{1-20}$-ketoalkyl-, —C(=O)—$C_6H_4$—, —$C_6H_4$—C(=O)—, —$C_6H_4$—, —$C_{10}H_6$—, —$C_6H_4$—$C_6H_4$—, —$C_{10}H_6$—$C_{10}H_6$—, —$C_6H_4$—O—$C_6H_4$—, —$C_{10}H_6$—O—$C_{10}H_6$—, and —$C_6H_4$—O—$C_6H_4$—O—$C_6H_4$—. In one preferred embodiment, $L^2$ and $L^4$ are the same. In another preferred embodiment, $L^2$, $L^3$ and $L^4$ are the same. In a further preferred embodiment, $L^3$ is a chemical bond. In yet a further preferred embodiment, $L^2$ and $L^4$ are the same and $L^3$ is a chemical bond. As used herein, the term "ketoalkyl" includes alkyls having one or more keto functionalities as in monoketo-alkyls, diketo-alkyls, and the like.

Exemplary optionally substituted $C_{5-30}$ aryl moieties useful in the compounds of formulas (1) and (1a) include, without limitation, pyridyl, phenyl, naphthyl, acenaphthyl, fluorenyl, carbazolyl, anthracenyl, phenanthryl, pyrenyl, coronenyl, tetracenyl, pentacenyl, tetraphenyl, benzotetracenyl, triphenylenyl, perylenyl, tolyl, xylyl, dibenzothiophenyl, thioxanthonyl, indolyl, acridinyl, and the like. In formula (1), each $Ar^1$ is independently any suitable optionally substituted $C_{5-30}$-aryl moiety. Preferably, each $Ar^1$ is unsubstituted $C_{5-30}$ aryl. Preferably, $Ar^1$ is chosen from pyridyl, phenyl, naphthyl, fluorenyl, carbazolyl, anthracenyl, phenanthryl, pyrenyl, coronenyl, tetracenyl, pentacenyl, tetraphenyl, triphenylenyl, perylenyl, indolyl, acridinyl, and more preferably from phenyl, naphthyl, fluorenyl, carbazolyl, anthracenyl, phenanthryl, pyrenyl, triphenylenyl, and perylenyl. In formula (1a), $Ar^2$ may be any unsubstituted $C_{5-30}$ aryl. Exemplary aryl moieties for $Ar^2$ include, without limitation, pyridyl, phenyl, naphthyl, acenaphthyl, fluorenyl, carbazolyl, anthracenyl, phenanthryl, pyrenyl, coronenyl, tetracenyl, pentacenyl, tetraphenyl, benzotetracenyl, triphenylenyl, perylenyl, dibenzothiophenyl, thioxanthonyl, indolyl, acridinyl, and the like. Preferably, $Ar^2$ is chosen from phenyl, naphthyl, fluorenyl, carbazolyl, anthracenyl, phenanthryl, pyrenyl, tetracenyl, pentacenyl, tetraphenyl, triphenylenyl, perylenyl, indolyl, and acridinyl, and more preferably from phenyl, naphthyl, fluorenyl, carbazolyl, anthracenyl, phenanthryl, pyrenyl, triphenylenyl, and perylenyl.

Preferred cyclopentadienone monomers of formula (1) include compounds of formula (1b) to (1k):

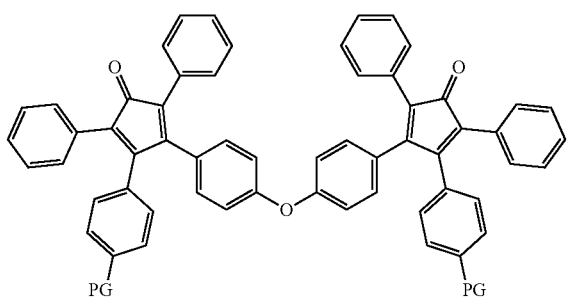

(1b) PG = $CO_2H$; (1c) PG = OH

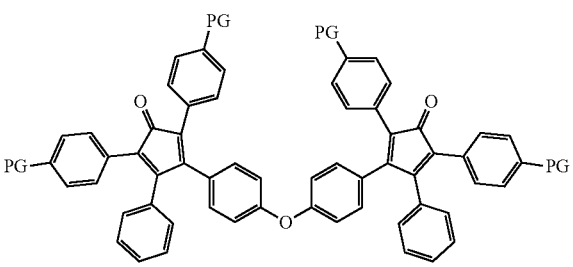

(1d) PG = $CO_2H$; (1e) PG = OH

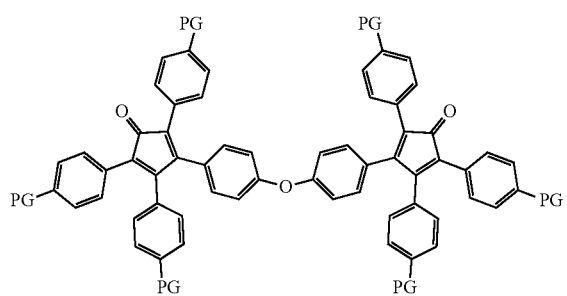

(1f) PG = $CO_2H$; (1g) PG = OH

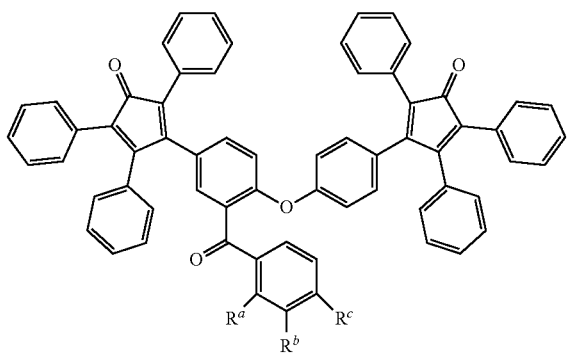

(1h) $R^a$ = -$CO_2H$, $R^b$ = $R^c$ = H;
(1i) $R^a$ = $R^b$ = -$CO_2H$, $R^c$ = H;
(1j) $R^a$ = H, $R^b$ = $R^c$ = -$CO_2H$ (1k)

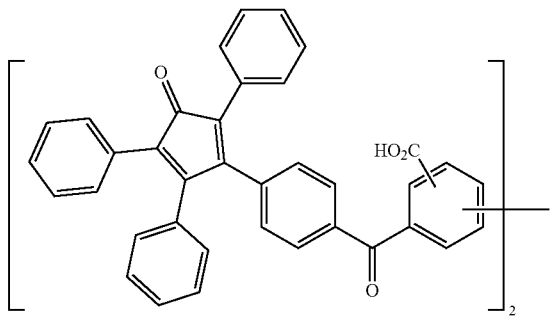

The present cyclopentadienone monomers may be prepared by a variety of procedures, such as by the condensation of benzils with benzyl ketones using conventional methods. Exemplary methods are disclosed in Kumar et al. Macromolecules, 1995, 28, 124-130; Ogliaruso et al., J. Org. Chem., 1965, 30, 3354; Ogliaruso et al., J. Org. Chem., 1963, 28, 2725; and U.S. Pat. No. 4,400,540. In a particular example, the present cyclopentadione monomers may be prepared by reacting an appropriately substituted 4,4'-oxydibenzil with an appropriately substituted diphenylacetone, such as by reacting 4,4'-oxydibenzil with diphenylacetone dicarboxylate, or by reacting 4,4'-oxydibenzil dicarboxylate with diphenylacetone dicarboxylate. Alternatively, present cyclopentadione monomers may be prepared by reacting 4,4'-oxydibenzil with diphenylacetone to make diphenylene oxide bis(triphenylcyclopentadienone) (DPO-CPD), followed by acylating the DPO-CPD with a suitably substituted aromatic compound, such as phthalic anhydride.

The present cyclopentadienone monomers are particularly useful in the preparation of polyarylene resins. As used herein, the terms "polyarylenes" and "polyarylene resins" are used interchangeably and refer to polymers having di- or higher-valent aryl moieties in the polymer backbone and are prepared by a Diels-Alder polymerization of one or more of the present cyclopentadienone first monomers and one or more polyalkynyl-substituted second monomers. Such polyarylenes may optionally contain one or more divalent linking groups in the polymer backbone. A wide variety of polyalkynyl-substituted monomers may be polymerized with the present cyclopentadienone monomers to form the present polyarylene resins, such as those polyalkynyl-substituted monomers disclosed in International Pat. App. No. WO 97/10193 and U.S. patent application Ser. No. 15/056,352 (Gilmore et al.), filed on Feb. 29, 2016. It is preferred that at least one polyalkynyl-substituted second monomers have the formula (2)

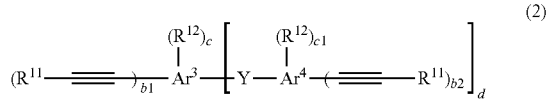

(2)

wherein each $Ar^3$ and $Ar^4$ is independently a $C_{5-30}$ aryl moiety; each $R^{11}$ is independently chosen from H, optionally substituted $C_{5-30}$-aryl, and $(PG-L^5)_{t2}-Ar^5-$; each $R^{12}$ is independently chosen from H, optionally substituted $C_{5-30}$ aryl, $C_{1-20}$-alkyl, $C_{1-20}$-haloalkyl, $C_{7-30}$-arylalkyl, and $-L^5-$PG; PG is a polar moiety; each $Ar^5$ is independently an optionally substituted $C_{5-30}$-aryl; $L^5$ is a single chemical bond or a divalent linking group; each $L^5$ is independently a single chemical bond or a divalent linking group, each Y is independently a single chemical bond or a divalent linking group chosen from $-O-$, $-S-$, $-S(=O)-$, $-S(=O)_2-$, $-C(=O)-$, $-(C(R^{13})_2)_z-$, $C_{6-30}$-aryl, and $-(C(R^{13})_2)_{z1}-(C_{6-30}\text{-aryl})-(C(R^{13})_2)_{z2}-$; each $R^{13}$ is independently chosen from H, hydroxy, halo, $C_{1-10}$-alkyl, $C_{1-10}$-haloalkyl, and optionally substituted $C_{6-30}$-aryl; $t2=1$ to 4; $b1=1$ to 4; each $b2=0$ to 2; $b1+$ each $b2=2$ to 6; $c=0$ to 4; each $c1=3$ to 5; $d=0$ to 2; $z=1$ to 10; $b1+c+d=6$; $z1=0$ to 10; $z2=0$ to 10; and $z1+z2=1$ to 10. It is preferred that each of $Ar^1$ and $Ar^2$ is independently a $C_{6-30}$-aryl. Preferably, $R^{11}$ is chosen from H, phenyl and $(PG-L^5)_{t2}-Ar^5-$, and more preferably H or phenyl. It is preferred that $R^{12}$ is H, $C_{6-10}$-aryl, $C_{1-10}$-alkyl, or PG, more preferably H, phenyl, $C_{1-10}$-alkyl, or PG, and yet more preferably H, phenyl, or PG. Preferably, each Y is independently a single chemical bond or a divalent linking group chosen from $-O-$, $-S-$, $-S(=O)-$, $-S(=O)_2-$, $-C(=O)-$, $-(C(R^{13})_2)_z-$, and $C_{6-30}$-aryl, and more preferably a chemical bond, $-O-$, $-S-$, $-S(=O)_2-$, $-C(=O)-$, and $-(C(R^{13})_2)_z-$. It is preferred that $b1=1$ to 2, and more preferably 2. It is preferred that each $b2=0$ or 1. Preferably, $b1+$ each $b2=2$ to 4, and more preferably 2 or 3, and even more preferably 2. It is preferred that $d=0$ or 1, and more preferably 0. It is further preferred that $b1=2$ or 3 and $d=0$. Preferably, $z=1$ to 6, more preferably 1 to 3, and even more preferably $z=1$. Preferably, each of $z1$ and $z2$ are 0 to 5. Preferably $z1+z2=1$ to 6, and more preferably 2 to 6. PG in formula (2) is as defined above in formula (1). Preferably, each PG in formula (2) is independently chosen from $-OR^4$, $C_{1-4}$-hydroxyalkyl, $-C(=O)OR^5$ and $-C(=O)N(R^6)_2$, yet more preferably from $-OH$ and $-C(=O)OR^5$, and even more preferably from $-OH$ and $-CO_2H$; where $R^4$, $R^5$, and $R^6$ are as defined above for formula (1).

It is preferred that $Ar^3$ and each $Ar^4$ in formula (2) are independently a $C_{6-20}$-aryl moiety. Suitable aryl moieties for $Ar^3$ and $Ar^4$ in formula (2) include, but are not limited to, pyridyl, phenyl, naphthyl, anthracenyl, phenanthryl, tetracenyl, pyrenyl, perylenyl, coronenyl, pentacenyl, triphenylenyl, tetraphenyl, benzotetracenyl, biphenyl, and binaphthyl. It is preferred that $Ar^3$ and each $Ar^4$ are independently chosen from phenyl, naphthyl, anthracenyl, phenanthryl, pyrenyl, tetracenyl, pentacenyl, tetraphenyl, triphenylenyl, and perylenyl, and more preferably from phenyl, naphthyl, anthracenyl, phenanthryl, and pyrenyl. In formula (2), $Ar^5$ is preferably $C_{6-30}$-aryl. Suitable aryl moieties for $Ar^5$ in formula (2) include, but are not limited to, pyridyl, phenyl, naphthyl, anthracenyl, phenanthryl, tetracenyl, pyrenyl, perylenyl, coronenyl, pentacenyl, triphenylenyl, tetraphenyl, benzotetracenyl, biphenyl, and binaphthyl. Preferably, each $Ar^5$ is independently chosen from phenyl, naphthyl, anthracenyl, phenanthryl, and pyrenyl.

$L^5$ in formula (2) is a single chemical bond or any divalent linking group suitable for linking polar moiety PG to $Ar^5$. It is preferred that $L^5$ is a single chemical bond or an organic radical having 1 to 30 carbon atoms, and more preferably a single chemical bond or an organic radical having 1 to 20 carbon atoms. The organic radical of $L^5$ may optionally contain one or more heteroatoms chosen from O, S, N, and combinations thereof, and preferably contains from 0 to 10 heteroatoms, and more preferably from 0 to 5 heteroatoms. Preferably, each $L^5$ is chosen from single chemical bond, $-O-$, $-S-$, $-S(=O)-$, $-S(=O)_2-$, optionally substituted $C_{5-30}$-aryl, optionally substituted $C_{1-30}$-alkyl such as $C_{1-30}$-ketoalkyl, optionally substituted $C_{1-10}$-alkyl-optionally substituted $C_{5-30}$-aryl such as $C_{1-10}$-ketoalkyl-$C_{5-30}$- aryl, and the like. More preferably, each $L^5$ is independently a single chemical bond, —O—, —S—, —S(=O)—, —S(=O)$_2$—, —C(=O)—C$_6$H$_4$—, —C(=O)—C$_{10}$H$_6$—, —C(=O)—C$_{16}$H$_8$—, —CH$_2$—C$_6$H$_4$—, —CH$_2$—C$_{10}$H$_6$—, —CH$_2$—C$_6$H$_4$—, —C$_2$H$_4$—C$_6$H$_4$—, —C$_6$H$_4$—, —C$_{10}$H$_6$—, —C$_{16}$H$_8$—, C$_{1-10}$-alkyl, C$_{1-10}$-keto alkyl, and C$_{1-10}$-heteroalkyl, and the like, even more preferably a single chemical bond, —O—, —C(=O)—, —CH$_2$C(=O)—, —CH$_2$C(=O)CH$_2$—, —C(=O)—C$_6$H$_4$—, —C(=O)—C$_{10}$H$_6$—, —C(=O)—C$_{16}$H$_8$—, —CH$_2$—C$_6$H$_4$—, —CH$_2$—C$_{10}$H$_6$—, —CH$_2$—C$_6$H$_4$—, —CH$_2$—C$_6$H$_4$—CH$_2$—, —C$_2$H$_4$—C$_6$H$_4$—, —C$_6$H$_4$—, —C$_{10}$H$_6$—, C$_{1-10}$-alkyl, and C$_{1-10}$-heteroalkyl and yet more preferably $L^5$ is a chemical bond.

Preferred polyalkynyl-substituted second monomers are those of formulas (2a) and (2b):

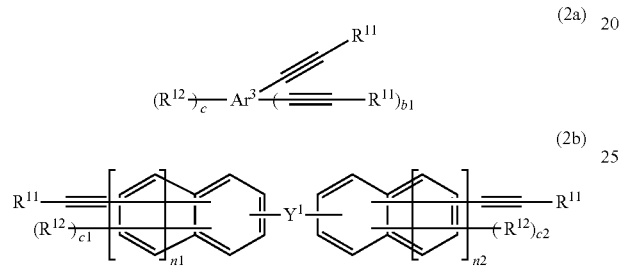

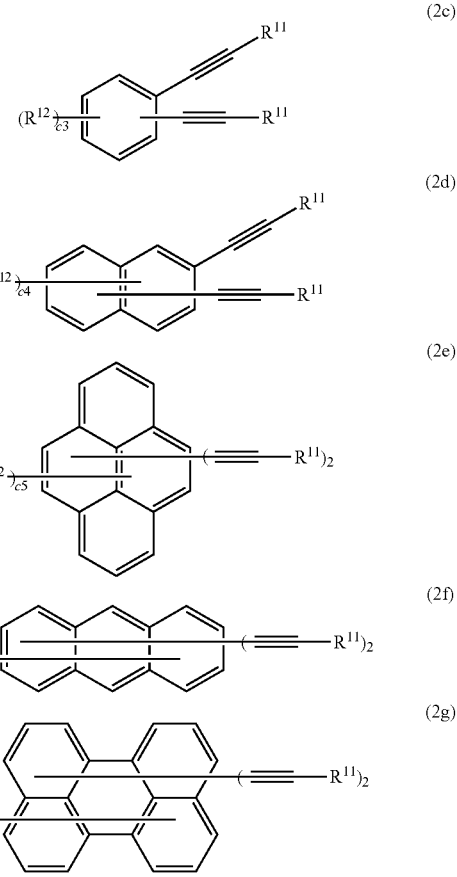

wherein $Ar^3$, $R^{11}$, $R^{12}$, b1 and c are as defined above for formula (2); c1 is 1 or 2; c2 is 0 to 2; each of n1 and n2 is independently 0 to 4; and $Y^1$ is a single chemical bond, O, S, S(=O)$_2$, C(=O), C(CH$_3$)$_2$, CF$_2$, and C(CF$_3$)$_2$. It will be appreciated by those skilled in the art that the brackets ("[ ]") in formula (2b) refer to the number of aromatic rings fused to the phenyl ring. Accordingly, when n1 (or n2)=0, the aromatic moiety is phenyl; when n1 (or n2)=1, the aromatic moiety is naphthyl; when n1 (or n2)=2, the aromatic moiety may be anthracenyl or phenanthryl; when n1 (or n2)=3, the aromatic moiety may be tetracenyl, tetraphenyl, triphenylenyl, or pyrenyl; and when n1 (or n2)=4, the aromatic moiety may be perylenyl or benzotetracenyl. In formula (2a), c is preferably 1 to 2, and more preferably c=1. It is preferred that b1 in formula (2a) is 1 or 2, and more preferably 1. It is preferred in formula (2a) and (2b) that $R^{11}$ is preferably H, phenyl, —C$_6$H$_4$OH, —C$_6$H$_4$C(=O)OH, —CH$_2$OH, or —C(=O)OH, and more preferably H, phenyl, —C$_6$H$_4$OH, or —C$_6$H$_4$C(=O)OH. $R^{12}$ in each of formulas (2a) and (2b) is preferably OH, C$_{1-6}$-hydroxyalkyl, C(=O)OH, —C(=O)N($R^{13}$)$_2$, —S(=O)$_2$—OH, and S(=O)$_2$—N($R^{13}$)$_2$, and more preferably OH and C(=O)OH. Each $R^{13}$ is independently chosen from H, C$_{6-10}$-aryl, and C$_{1-20}$-alkyl, and preferably from H, and C$_{1-20}$-alkyl. $Ar^3$ in formula (2a) is preferably phenyl, naphthyl, anthracenyl, pyrenyl, and perylenyl. In formula (2b), it is preferred that n1 and n2 are independently chosen from 0, 1, 2, 3, and 4, more preferably from 0, 1, 2 and 3, and even more preferably from 1,2 and 3. It is further preferred that n1=n2. In formula (2b), $Y^1$ is preferably a single chemical bond, O, S(=O)$_2$, C(=O), C(CH$_3$)$_2$, CF$_2$, and C(CF$_3$)$_2$, and more preferably a chemical bond.

Particularly preferred polyalkynyl-substituted second monomers of formula (2) are monomers of formulas (2c) to (2g):

wherein $R^{11}$ and $R^{12}$ are as described above; c3=1 or 2; and each of c4, c5, c6, and c7 are independently 1 to 4. Preferably, c3=1. It is preferred that c4 is 1 to 3, more preferably 1 or 2, and even more preferably 1. Preferably, each of c5 to c7 is independently 1 to 3, and more preferably 1 to 2.

In the polyalkynyl-substituted second monomers of formula (2), any two alkynyl moieties may have an ortho, meta or para relationship to each other, and preferably a meta or para relationship to each other. Preferably, the alkynyl moieties in the monomers of formula (2) do not have an ortho relationship to each other.

Compounds useful as the polyalkynyl-substituted second monomers of formula (2) are generally commercially available, or may be prepared by methods known in the art. Preferred monomers of formula (2) are: 1,3-diethynylbenzene; 1,4-diethynylbenzene; 4,4'-diethynyl-1,1'-biphenyl; 3,5-diethynyl-1,1'-biphenyl; 1,3,5-triethynylbenzene; 1,3-diethynyl-5-(phenylethynyl)benzene; 1,3-bis(phenylethynyl)benzene; 1,4-bis(phenylethynyl)benzene; 1,3,5-tris(phenylethynyl)benzene; 4,4'-bis(phenylethynyl)-1,1'-biphenyl; 4,4'-diethynyl-diphenylether; and mixtures thereof. More preferably, the monomers of formula (2) are chosen from: 1,3-diethynylbenzene; 1,4-diethynylbenzene; 1,3,5-triethynylbenzene; 4,4'-diethynyl-1,1'-biphenyl; 1,3-bis(phenylethynyl)-benzene; 1,4-bis(phenylethynyl)benzene; 4,4'-bis(phenylethynyl)-1,1'-biphenyl; 1,3,5-tris(phenylethynyебenzene; 3,5-bis(phenylethynyl)benzoic acid; 3,5-diethynylbenzenesulfonic acid; 6,6'-diethynyl-[1,1'-binaphthalene]-2,2'-diol; 3,5-diethynylphenol; 4,9-diethynylpyrene-1,6-diol; 9,10-diethynylanthracene-2,6-diol;

5,8-diethynylperylene-1,12-diol; 4,9-diethynylpyrene-1,6-dicarboxylic acid; 3,5-bis(phenylethynyl)benzoic acid; and mixtures thereof. Even more preferably, the polyalkynyl-substituted second monomers are chosen from: 1,3-diethynylbenzene; 1,4-diethynylbenzene; 4,4'-diethynyl-1,1'-biphenyl; 1,3,5-triethynylbenzene; 1,3,5-tris(phenylethynyl)benzene; 3,5-bis(phenylethynyl)benzoic acid; 3,5-diethynylbenzenesulfonic acid; 6,6'-diethynyl-[1,1'-binaphthalene]-2,2'-diol; 3,5-diethynylphenol; 4,9-diethynylpyrene-1,6-diol; 9,10-diethynylanthracene-2,6-diol; 5,8-diethynylperylene-1,12-diol; 4,9-diethynylpyrene-1,6-dicarboxylic acid; 3,5-bis(phenylethynyl)benzoic acid and mixtures thereof.

The present polyarylene resins may be comprised of one monomer of formula (1), or a mixture of two or more monomers of formula (1). Monomers of formula (2) are preferred second monomers. It is preferred that the present polyarylene polymers are comprised of polymerized units of one or more monomers of formula (1) and one or more polyalkynyl-substituted second monomers, where at least one polyalkynyl-substituted second monomer has the formula (2). Mixtures of resins comprising as polymerized units one or more monomers of formula (1) and one or more monomers of formula (2) are preferred.

The present polyarylene resins may further comprise one or more cyclopentadienone monomers comprising 2 or more cyclopentadienone moieties, said cyclopentadienone moieties and being free of a polar moiety. Such monomers are well-known in the art, such as those described in U.S. Pat. Nos. 5,965,679; 6,288,188; and 6,646,081; and in Int. Pat. Pubs. WO 97/10193 and WO 2004/073824. Preferably, such optional cyclopentadienone monomers comprise 2 to 4 cyclopentadienone moieties, more preferably 2 or 3 cyclopentadienone moieties, and most preferably two cyclopentadienone moieties. It is preferred that the optional cyclopentadienone monomer has the structure shown in formula (3)

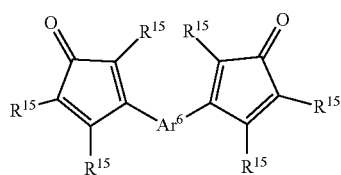
(3)

wherein each $R^{15}$ is independently chosen from H, $C_{1-6}$-alkyl, or optionally substituted $C_{5-30}$-aryl; and $Ar^6$ is an aromatic moiety having from 5 to 60 carbon atoms. Preferably, each $R^{15a}$ is independently chosen from $C_{3-6}$ alkyl, phenyl and substituted phenyl, and more preferably each $R^{15}$ is phenyl. As used herein, "substituted phenyl" refers to a phenyl moiety substituted with one or more of halogen, $C_{1-10}$-alkyl, $C_{5-10}$-aryl. A wide variety of aromatic moieties are suitable for use as $Ar^6$, such as those disclosed in U.S. Pat. No. 5,965,679. Exemplary aromatic moieties useful for $Ar^3$ include those having the structure shown in formula (4)

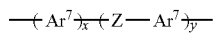
(4)

wherein x is an integer chosen from 1, 2 or 3; y is an integer chosen from 0, 1, or 2; each $Ar^7$ is independently chosen from

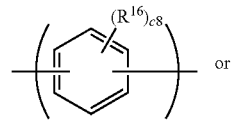
(5)

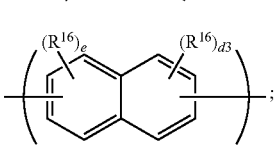
(6)

each $R^{16}$ is independently chosen from halogen, $C_{1-6}$-alkyl, $C_{1-6}$-haloalkyl, $C_{1-6}$-alkoxy, $C_{1-6}$-haloalkoxy, phenyl, and phenoxy; c8 is an integer from 0 to 4; each of d3 and e is independently an integer from 0 to 3; each Z is independently chosen from a chemical bond, O, S, $NR^{17}$, $PR^{17}$, $P(=O)R^{17}$, $C(=O)$, $CR^{18}R^{19}$, and $SiR^{18}R^{19}$; $R^{17}$, $R^{18}$, and $R^{19}$ are independently chosen from H, $C_{1-4}$-alkyl, $C_{1-4}$-haloalkyl, and phenyl. It is preferred that x is 1 or 2, and more preferably 1. It is preferred that y is 0 or 1, and more preferably 1. Preferably, each $R^{16}$ is independently chosen from halogen, $C_{1-4}$-alkyl, $C_{1-4}$-haloalkyl, $C_{1-4}$-alkoxy, $C_{1-4}$-haloalkoxy, and phenyl, and more preferably from fluoro, $C_{1-4}$-alkyl, $C_{1-4}$-fluoroalkyl, $C_{1-4}$-alkoxy, $C_{1-4}$-fluoroalkoxy, and phenyl. It is preferred that c8 is from 0 to 3, more preferably from 0 to 2, and yet more preferably 0 or 1. It is preferred that each of d3 and e is independently 0 to 2, and more preferably 0 or 1. In formula (6), it is preferred that d3+e=0 to 4, and more preferably 0 to 2. Each Z is preferably independently chosen from O, S, $NR^{17}$, $C(=O)$, $CR^{18}R^{19}$, and $SiR^{18}R^{19}$, more preferably from O, S, $C(=O)$, and $CR^{18}R^{19}$, and yet more preferably from O, $C(=O)$, and $CR^{18}R^{19}$. It is preferred that each $R^{17}$, $R^{18}$, and $R^{19}$ are independently chosen from H, $C_{1-4}$-alkyl, $C_{1-4}$-fluoroalkyl, and phenyl; and more preferably from H, $C_{1-4}$-alkyl, $C_{1-2}$-fluoroalkyl, and phenyl. Preferably, each $Ar^7$ has the formula (5).

Optionally, one or more end capping monomers may be used to prepare the present polyarylene resins. Such end capping monomers have a single alkyne moiety and a solubility improving polar group and which function to cap one end, preferably two ends, and more preferably all ends, of the present polymers. Suitable end capping monomers are those disclosed in U.S. Pub. Pat. App. No. 2016/0060393 (Gilmore et al.). Preferably, the polar moieties present in these optional end capping monomers are cleavable under conditions used to cure the present polyarylene polymers. Suitable optional end capping monomers are those of formula (7):

(7)

wherein $R^{20}$ is H, optionally substituted $C_{1-10}$-alkyl, optionally substituted $C_{7-12}$-aralkyl, optionally substituted $C_{6-10}$-aryl, or $R^{21}$; and $R^{21}$ is a polar moiety. Suitable polar moieties are any hydrocarbyl moiety having from 1 to 20 carbon atoms and one or more functional groups chosen from $—C(=O)—R^{22}$, $—C(=O)OR^{22}$, $—OH$, $—NO_2$, and $—NR^{22}R^{23}$, where $R^{22}$ and $R^{23}$ are independently chosen from H, $C_{1-10}$-alkyl, $C_{7-16}$-aralkyl, and $C_{6-10}$-aryl. Preferably, the polar moiety of formula (7) is chosen from $—C(=O)—R^{22}$, $—C(=O)OR^{22}$, $—OH$, and $—NR^{22}R^{23}$, and more preferably from —C(=O)—R$^{22}$, —C(=O)OR$^{22}$, and —OH. Such —C(=O)—, —OH, and —NR$^{22}$R$^{23}$ functional groups may be part of another functional group, as in carboxylic acids, anhydrides, amides, ketones, esters, and the like. It is preferred that the polar moiety is chosen from carboxyl, $C_{2-12}$-aliphatic carboxylate, $C_{1-10}$-hydroxyalkyl, $C_{6-10}$-hydroxyaryl, $C_{7-20}$-aryl carboxylic acid, $C_{8-20}$-aryl carboxylic acid anhydride, $C_{7-20}$-aryl carboxylates, $C_{7-20}$-aryl amide, $C_{8-20}$-aryl imide, amino-$C_{1-10}$-alkyl, and $C_{6-20}$-aryl amine. More preferably, the polar moiety of formula (7) is chosen from carboxyl, $C_{2-12}$-aliphatic carboxylate, hydroxy-$C_{1-10}$-alkyl, hydroxy-$C_{6-10}$-aryl, $C_{7-16}$-aryl carboxylic acid, and $C_{8-16}$-aryl carboxylic acid anhydride. Exemplary end capping monomers are: propiolic acid; acetylene dicarboxylic acid; phenyl propiolic acid; ethynyl benzoic acid; ethynyl phthalic acid; propargyl alcohol; propargyl amine; 2-butyn-1,4-diol; 2-methyl-3-butyn-2-ol; 3-butyn-1-ol; 3-butyn-2-ol; 2-butyn-1-ol; 2-butynoic acid; ethynyl phenol; xylityl propiolate; ethynyl phthalic anhydride; ethynyl phthalimide; ethynyl benzamide; 2-butyn-1,4-diol diacetate; 3-butyn-2-one; 1-ethynyl-1-cyclohexanol; 1-ethynylcyclohexylamine; 1-ethynylcyclopentanol; ethynylaniline; N-(ethynylphenyl)acetamide; 2-carbamoyl-5-ethynylbenzoic acid; ethynyl-nitrobenzene; propiolamide; N-hydroxylpropiolamide; 2-aminobut-3-ynoic acid; and mixtures thereof. Preferred end capping monomers are: propiolic acid; acetylene dicarboxylic acid; phenyl propiolic acid; ethynyl benzoic acid; ethynyl phthalic acid; propargyl alcohol; 2-butyn-1,4-diol; 2-methyl-3-butyn-2-ol; 3-butyn-1-ol; 3-butyn-2-ol; 2-butyn-1-ol; 2-butynoic acid; ethynyl phenol; xylityl propiolate; ethynyl phthalic anhydride; 2-butyn-1,4-diol diacetate; and mixtures thereof. Such end capping monomers are generally commercially available, or may be prepared by methods known in the art.

The polyarylene resins of the present invention are prepared by reacting one or more first monomers of formula (1), one or more polyalkynyl-substituted second monomers, and optionally one or more additional monomers, such as the optional monomers of formulas (3) and/or (7) discussed above, in a suitable organic solvent. The mole ratio of the total first monomers (that is, monomers containing two cyclopentadienone moieties) to the total second monomers (that is, monomers containing two or more alkyne moieties) 1.95:1 to 1:1.2, and preferably from 1.75:1 to 1:1.15. When an optional third monomer is used, the mole ratio of the total first monomer to the total third monomer is from 0.1:1 to 1:0.1, preferably from 0.25:1 to 1:0.25, more preferably from 0.3:1 to 1:0.3, yet more preferably from 0.5:1 to 1:0.5, and even more preferably from 0.4:0.6 to 0.75:0.25. When an optional end capping monomer is used, it is typically used in a total amount of from 0.05 to 0.25 moles, based on 1 mole of the first monomer, preferably from 0.075 to 0.2 moles, and more preferably from 0.09 to 0.125 moles.

Suitable organic solvents useful to prepare the present resins are benzyl esters of $C_{2-6}$-alkanecarboxylic acids, dibenzyl esters of $C_{2-6}$-alkanedicarboxylic acids, tetrahydrofurfuryl esters of $C_{2-6}$-alkanecarboxylic acids, ditetrahydrofurfuryl esters of $C_{2-6}$-alkanedicarboxylic acids, phenethyl esters of $C_{2-6}$-alkanecarboxylic acids, diphenethyl esters of $C_{2-6}$-alkanedicarboxylic acids, aromatic ethers, aromatic hydrocarbons, cyclic hydrocarbons, carbonates, and lactones. Preferred aromatic ethers are diphenyl ether, dibenzyl ether, $C_{1-6}$-alkoxy-substituted benzenes and benzyl $C_{1-6}$-alkyl ethers, and more preferably $C_{1-4}$-alkoxy-substituted benzenes and benzyl $C_{1-6}$-alkyl ethers. Preferred organic solvents are benzyl esters of $C_{2-6}$-alkanecarboxylic acids, dibenzyl esters of $C_{2-6}$-alkanedicarboxylic acids, tetrahydrofurfuryl esters of $C_{2-6}$-alkanecarboxylic acids, ditetrahydrofurfuryl esters of $C_{2-6}$-alkanedicarboxylic acids, phenethyl esters of $C_{2-6}$-alkanecarboxylic acids, diphenethyl esters of $C_{2-6}$-alkanedicarboxylic acids, $C_{1-6}$-alkoxy-substituted benzenes, and benzyl $C_{1-6}$-alkyl ethers, more preferably benzyl esters of $C_{2-6}$-alkanecarboxylic acids, tetrahydrofurfuryl esters of $C_{2-6}$-alkanecarboxylic acids, phenethyl esters of $C_{2-6}$-alkanecarboxylic acids, $C_{1-4}$-alkoxy-substituted benzenes, benzyl $C_{1-4}$-alkyl ethers, dibenzyl ether, carbonates, and lactones, and yet more preferably benzyl esters of $C_{2-6}$-alkanecarboxylic acids, tetrahydrofurfuryl esters of $C_{2-6}$-alkanecarboxylic acids, $C_{1-4}$-alkoxy-substituted benzenes, benzyl $C_{1-4}$-alkyl ethers, carbonates, and lactones. Exemplary organic solvents include, without limitation, benzyl acetate, benzyl propionate, tetrahydrofurfuryl acetate, tetrahydrofurfuryl propionate, tetrahydrofurfuryl butyrate, anisole, methylanisole, dimethylanisole, dimethoxybenzene, ethylanisole, ethoxybenzene, xylene, mesitylene, cumene, limonene, benzyl methyl ether, benzyl ethyl ether, and propylene carbonate, and preferably benzyl acetate, benzyl proprionate, tetrahydrofurfuryl acetate, tetrahydrofurfuryl propionate, tetrahydrofurfuryl butyrate, anisole, methylanisole, dimethylanisole, dimethoxybenzene, ethylanisole, ethoxybenzene, xylene, mesitylene, cumene, limonene, propylene carbonate, and gamma-butyrolactone.

The resins of the present invention may be prepared by combining one or more first monomers, one or more second monomers, optionally one or more other monomers, and organic solvent, each as described above, in any order in a vessel, and heating the mixture. The first monomer may be combined with the organic solvent in a vessel, and then the second monomer and any optional additional monomers are added to the mixture. In one embodiment, the first monomer and organic solvent mixture is heated to the desired reaction temperature before the second monomer is added. The second monomer may be added over a period of time, such as from 0.25 to 48 hours, and preferably from 1 to 6 hours, to reduce exotherm formation, but is preferably added at one time. The first monomer and organic solvent mixture may be heated to the desired reaction temperature before the second monomer and any optional monomers are added. Alternatively, the first monomer, second monomer, optional other monomers, and solvent are added to a vessel, and then heated to the desired reaction temperature and held at this temperature for a period of time to provide the desired polymer. The reaction mixture is heated at a suitable temperature, such as from 85 to 215° C., and preferably from 90 to 205° C. The first and second monomers may react at temperatures below those conventionally used to make polyarylene polymers by a Diels-Alder type reaction. While not wishing to be bound by theory, it is believed that the presence of certain solubility enhancing moieties may activate the monomer such that the Diels-Alder reaction is facilitated at a lower temperature. The reaction may be carried out under oxygen-containing atmosphere, but an inert atmosphere is preferred. Following the reaction, the resulting polymer may be isolated from the reaction mixture, diluted with appropriate solvent, or used as is for coating a surface. When a second monomer having two alkynyl moieties having terminal hydrogens and one alkynyl moiety having a terminal phenyl group is used to prepare the present polymers, heating the monomer reaction mixture at a temperature of 90 to 130° C. will provide an oligomer where substantially only the alkynyl moieties having terminal hydrogens react with the first monomer to form a linear oligomer having 1 or 2 third monomers as end caps, that is, the alkynyl moieties having the terminal phenyl group remain substantially unreacted (<10%, and preferably <5%, of such groups react).

The present polyarylene resins may have any suitable molecular weight range, such as a weight average molecular weight ($M_w$) of from 500 to 250000 Da (as determined by gel permeation chromatography against polystyrene standards), preferably from 1000 to 100000 Da, and more preferably from 3000 to 25000 Da. The choice of organic solvent can be used to tailor the $M_w$ of the resulting resin. For example, when aromatic ether solvents, such as $C_{1-6}$-alkoxy-substituted benzenes, are used, relatively higher $M_w$ oligomers may be obtained as compared to resins having a relatively lower $M_w$ when the same reaction is performed using a benzyl ester of a $C_{2-6}$-alkanecarboxylic acid as the organic solvent. The molecular weight of the present resins can also be controlled, even in aromatic ether solvents, by adjusting the amount of the first monomer and/or optional monomers. For example, to obtain a resin having a $M_w$ of ≤35000, >1.05 mole of the first monomer should be used for each 1 mole of the second monomer, that is, the mole ratio of total cyclopentadienone monomers to total polyalkynyl-substituted monomers should be 1: ≥1.05, such as from 1:1.075 to 1:1.95. As the optional end capping monomer, such as the monomers of formula (7), has a single alkynyl moiety, it can be used to control the growth of the polymer chain. Increasing the total amount of any end capping monomer in the reaction will generally provide resins having relatively lower weight average molecular weights ($M_w$), while decreasing the total amount of any end capping monomer will provide resins having relatively higher M.

While not intending to be bound by theory, it is believed that the present polyarylene resins are formed through the Diels-Alder reaction of the cyclopentadienone moieties of the first monomer with the alkynyl moieties of the second monomer and the alkynyl moieties of any optional end capping monomers upon heating. During such Diels-Alder reaction, a carbonyl-bridged species forms. It will be appreciated by those skilled in the art that such carbonyl-bridged species may be present in the resins. Upon further heating, the carbonyl bridging species will be essentially fully converted to an aromatic ring system. Due to the mole ratio of the monomers used, the present resins contain arylene rings pendent from the polymer, or in the polymer backbone, or both which are substituted with at least one solubility enhancing polar moiety as illustrated in reaction scheme 1, where A is the first monomer, B is the second monomer, L is a linking group and PG is the polar moiety. The present resins may be composed of polymer chains that terminate with cyclopentadienone and/or alkyne moieties, depending on the particular mole ratio of first monomers (and any optional third monomers) to second monomers. It will be appreciated by those skilled in the art that when end capping monomers are used, the present resins will be composed of polymer chains that generally do not terminate with cyclopentadienone moieties.

Scheme 1

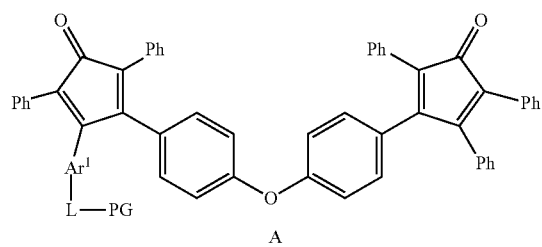

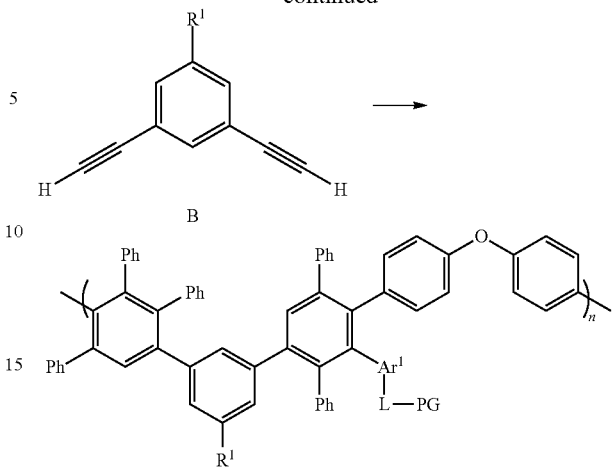

Coating compositions of the invention comprise one or more polyarylene resins described above and one or more organic solvents. The present resins in the organic reaction solvent can be directly cast as a film, applied as a coating or poured into a non-solvent to precipitate the resin. Water, methanol, ethanol and other similar polar liquids such as glycol ethers are typical non-solvents which can be used to precipitate the resin. Solid resin may be dissolved and processed from a suitable organic solvent described above, or from organic solvents typically used in the electronics industry. Preferred organic solvents useful in the present coating compositions are propylene glycol methyl ether (PGME), propylene glycol methyl ether acetate (PGMEA), methyl 3-methoxypropionate (MMP), ethyl lactate, n-butyl acetate, anisole, N-methyl pyrrolidone, gamma-butyrolactone (GBL), ethoxybenzene, benzyl propionate, benzyl benzoate, propylene carbonate, methyl 2-hydroxyisobutyrate, cyclohexanone, and mixtures thereof. Mixtures of organic solvents are particularly preferred, such as a mixture comprising one or more of anisole, ethoxybenzene, PGME, PGMEA, GBL, MMP, n-butyl acetate, benzyl propionate and benzyl benzoate in combination with one or more additional organic solvents, and more preferably a mixture comprising two or more of anisole, ethoxybenzene, PGME, PGMEA, GBL, MMP, n-butyl acetate, benzyl propionate, and benzyl benzoate. When a mixture of solvents is used, the ratio of solvents is generally not critical and may vary from 99:1 to 1:99 w/w. The solubility enhancing polar moieties pendent from the backbone of the present resins provide improved solubility as compared to polyarylene resins without such solubility enhancing moieties. It will be appreciated by those skilled in the art that the concentration of the resin in the organic reaction solvent may be adjusted by removing a portion of the organic solvent, or by adding more of the organic solvent, as may be desired.

Optionally, the present coating compositions may further comprise one or more additives, such as additives chosen from curing agents, crosslinking agents, and surface leveling agents. The selection of such optional additives and their amounts are well within the ability of those skilled in the art. Curing agents are typically present in an amount of from 0 to 20 wt % based on total solids, and preferably from 0 to 3 wt %. Crosslinking agents are typically used in an amount of from 0 to 30 wt % based on total solids, and preferably from 3 to 10 wt %. Surface leveling agents are typically used in an amount of from 0 to 5 wt % based on total solids, and preferably from 0 to 1 wt %. The selection of such optional additives and their amounts used are within the ability of those skilled in the art.

Curing agents may optionally be used in the coating compositions to aid in the curing of the deposited polyarylene resin film. A curing agent is any component which causes curing of the polymer on the surface of a substrate. Preferred curing agents are acids and thermal acid generators. Suitable acids include, but are not limited to: arylsulfonic acids such as p-toluenesulfonic acid; alkyl sulfonic acids such as methanesulfonic acid, ethanesulfonic acid, and propanesulfonic acid; perfluoroalkylsulfonic acids such as trifluoromethanesulfonic acid; and perfluoroarylsulfonic acids. A thermal acid generator is any compound which liberates acid upon exposure to heat. Thermal acid generators are well-known in the art and are generally commercially available, such as from King Industries, Norwalk, Conn. Exemplary thermal acid generators include, without limitation, amine blocked strong acids, such as amine blocked sulfonic acids such as amine blocked dodecylbenzenesulfonic acid. It will also be appreciated by those skilled in the art that certain photoacid generators are able to liberate acid upon heating and may function as thermal acid generators.

The present coating compositions may optionally include one or more surface leveling agents (or surfactants). While any suitable surfactant may be used, such surfactants are typically non-ionic. Exemplary non-ionic surfactants are those containing an alkyleneoxy linkage, such as ethyleneoxy, propyleneoxy, or a combination of ethyleneoxy and propyleneoxy linkages.

In general, the present compositions comprise a polyarylene resin of the invention, an organic solvent, and one or more optional aditives, each as described above, wherein the resin is typically present in an amount of 1 to 35% solids, and preferably from 5 to 15% solids. Such compositions can be used to deposit a resin coating layer on a substrate. The thickness of the resin coating layer may vary from 50 nm to 500 µm, although such coatings may be thicker or thinner than this ranges depending on the particular application.

The present invention provides a method of manufacturing an electronic device comprising providing a substrate; coating a layer of the polyarylene resin composition described above on a surface of the substrate; removing any organic solvent; and curing the polyarylene resin to form a dielectric material layer. The present polyarylene compositions may be coated on an electronic device substrate by any suitable means, such as spin-coating, slot-die coating, doctor blading, curtain coating, roller coating, spray coating, dip coating, and the like. Spin-coating is preferred. In a typical spin-coating method, the present compositions are applied to a substrate which is spinning at a rate of 500 to 4000 rpm for a period of 15 to 90 seconds to obtain a desired layer of the aromatic resin reaction product on the substrate. It will be appreciated by those skilled in the art that the thickness of the aromatic resin layer may be adjusted by changing the spin speed, the solids content in the composition, and the like.

A wide variety of electronic device substrates may be used in the present invention, such as: packaging substrates such as multichip modules; flat panel display substrates; integrated circuit substrates; substrates for light emitting diodes (LEDs) including organic light emitting diodes (OLEDs); semiconductor wafers; polycrystalline silicon substrates; and the like. Such substrates are typically composed of one or more of silicon, polysilicon, silicon oxide, silicon nitride, silicon oxynitride, silicon germanium, gallium arsenide, aluminum, sapphire, tungsten, titanium, titanium-tungsten, nickel, copper, and gold. Suitable substrates may be in the form of wafers such as those used in the manufacture of integrated circuits, optical sensors, flat panel displays, integrated optical circuits, and LEDs. As used herein, the term "semiconductor wafer" is intended to encompass "an electronic device substrate," "a semiconductor substrate," "a semiconductor device," and various packages for various levels of interconnection, including a single-chip wafer, multiple-chip wafer, packages for various levels, or other assemblies requiring solder connections. Such substrates may be any suitable size. Preferred wafer substrate diameters are 200 mm to 300 mm, although wafers having smaller and larger diameters may be suitably employed according to the present invention. As used herein, the term "semiconductor substrate" includes any substrate having one or more semiconductor layers or structures which may optionally include active or operable portions of semiconductor devices. A semiconductor device refers to a semiconductor substrate upon which at least one microelectronic device has been or is being batch fabricated.

Optionally, a layer of an adhesion promoter may be applied to the substrate surface before the deposition of the polyarylene resin layer, which is subsequently cured to form the crosslinked polyarylene film. If it is desired to use an adhesion promoter, any suitable adhesion promoter for polyarylene films may be used, such as silanes, preferably organosilanes such as trimethoxyvinylsilane, triethoxyvinylsilane, hexamethyldisilazane $[CH_3)_3Si—NH—Si(CH_3)_3]$, or an aminosilane coupler such as gamma-aminopropyltriethoxysilane, or a chelate such as aluminum monoethylacetoacetatedi-isopropylate $[((i-C_3H_7O)_2Al(OCOC_2H_5CHCOCH_3))]$. In some cases, the adhesion promoter is applied from 0.01 to 5 wt % solution, excess solution is removed, and then the polyarylene oligomer is applied. In other cases, for example, a chelate of aluminum monoethylacetoacetatedi-isopropylate, can be incorporated onto a substrate by spreading a toluene solution of the chelate on a substrate and then baking the coated substrate at 350° C. for 30 min in air to form a very thin (for example 5 nm) adhesion promoting layer of aluminum oxide on the surface. Other means for depositing aluminum oxide are likewise suitable. Alternatively, the adhesion promoter, in an amount of, for example, from 0.05 to 5 wt % based on the weight of the monomer, can be blended with the monomers before polymerization, negating the need for formation of an additional layer. Particularly suitable adhesion promoters include those sold under the AP 3000, AP 8000, and AP 9000S designations, available from Dow Electronic Materials (Marlborough, Mass.).

After being coated on the substrate, the polyarylene resin layer is optionally baked at a relatively low temperature to remove any organic solvent and other relatively volatile components from the layer. Typically, the substrate is baked at a temperature of 90 to 140° C., although other suitable temperatures may be used. The baking time is typically from 10 seconds to 10 minutes, and preferably from 30 seconds to 5 minutes, although longer or shorter times may be used. When the substrate is a wafer, such baking step may be performed by heating the wafer on a hot plate. Following solvent removal, a layer, film or coating of the resin on the substrate surface is obtained.

When used as an underlayer, the polyarylene resin layer is then sufficiently cured such that the film does not intermix with a subsequently applied coating layer, such as a photoresist or other layer coated directly on the aromatic underlayer. The polyarylene resin underlayer may be cured in an oxygen-containing atmosphere, such as air, or in an inert atmosphere, such as nitrogen, and preferably in an oxygen-containing atmosphere. The curing conditions used are those sufficient to cure the film such that it does not intermix with a subsequently applied organic layer, such as a photoresist layer, while still maintaining the desired antireflective properties (n and k values) and etch selectivity of the underlayer film. This curing step is conducted preferably on a hot plate-style apparatus, though oven curing may be used to obtain equivalent results. Typically, such curing is performed by heating the polyarylene resin layer at a curing temperature of ≥250° C., preferably ≥350° C., and more preferably ≥400° C. The curing temperature selected should be sufficient to cure the polyarylene resin underlayer. Such curing step may take from 10 sec. to 10 min., preferably from 1 to 3 min., and more preferably from 1 to 2 min., although other suitable times may be used.

The initial baking step may not be necessary if the curing step is conducted in such a way that rapid evolution of any solvent and curing by-products is not allowed to disrupt the underlayer film quality. For example, a ramped bake beginning at relatively low temperatures and then gradually increasing to a temperature of ≥300° C. can give acceptable results. It can be preferable in some cases to have a two-stage curing process, with the first stage being a lower bake temperature of less than 200° C., and the second stage being a higher bake temperature of ≥300° C. Two stage curing processes facilitate uniform filling and planarization of pre-existing substrate surface topography, for example filling of trenches and vias.

After curing of the polyarylene resin underlayer, one or more processing layers, such as photoresists, silicon-containing layers, hardmask layers, bottom antireflective coating (or BARC) layers, and the like, may be coated on the cured underlayer. For example, a photoresist may be coated, such as by spin coating, directly on the surface of a silicon-containing layer or other middle layer which is directly on the resin underlayer, or, alternatively, the photoresist may be coated directly on the cured polyarylene resin underlayer. A wide variety of photoresists may be suitably used, such as those used in 193 nm lithography, such as those sold under the EPIC™ brand available from Dow Electronic Materials (Marlborough, Mass.). Suitable photoresists may be either positive tone development or negative tone development resists. Following coating, the photoresist layer is then imaged (exposed) using patterned actinic radiation, and the exposed photoresist layer is then developed using the appropriate developer to provide a patterned photoresist layer. The pattern is next transferred from the photoresist layer to the underlayers by an appropriate etching techniques. Typically, the photoresist is also removed during such etching step. Next, the pattern is transferred to the substrate and the underlayer removed by appropriate etching techniques known in the art, such as by plasma etching. Following patterning of the substrate, the underlayer is removed using conventional techniques. The electronic device substrate is then processed according to conventional means.

The cured polyarylene resin underlayer may be used as the bottom layer of a multilayer resist process. In such a process, a layer of the polyarylene resin is coated on a substrate and cured as described above. Next, one or more middle layers are coated on the polyarylene resin underlayer. For example, a silicon-containing layer or a hardmask layer is coated directly on the polyarylene resin underlayer. Exemplary silicon-containing layers include a silicon-BARC, which may be spin coated on the underlayer followed by curing, or an inorganic silicon layer such as SiON or $SiO_2$ which may be deposited on the underlayer by chemical vapor deposition (CVD). Any suitable hardmask may be used and may be deposited on the underlayer by any suitable technique, and cured as appropriate. Optionally, an organic BARC layer may be disposed directly on the silicon-containing layer or hardmask layer, and appropriately cured. Next, a photoresist, such as those used in 193 nm lithography, is coated directly on the silicon-containing layer (in a trilayer process) or directly on the organic BARC layer (in a quadlayer process). The photoresist layer is then imaged (exposed) using patterned actinic radiation, and the exposed photoresist layer is then developed using the appropriate developer to provide a patterned photoresist layer. The pattern is next transferred from the photoresist layer to the layer directly below it, by appropriate etching techniques known in the art, such as by plasma etching, resulting in a patterned silicon-containing layer in a trilayer process and a patterned organic BARC layer in a quadlayer process. If a quadlayer process is used, the pattern is next transferred from the organic BARC layer to the silicon-containing layer or hardmask layer using appropriate pattern transfer techniques, such as plasma etching. After the silicon-containing layer or hardmask layer is patterned, the aromatic resin underlayer is then patterned using appropriate etching techniques, such as $O_2$ or $CF_4$ plasma. Any remaining patterned photoresist and organic BARC layers are removed during etching of the polyarylene resin underlayer. Next, the pattern is transferred to the substrate, such as by appropriate etching techniques, which also removes any remaining silicon-containing layer or hardmask layer, followed by removal of any remaining patterned polyarylene resin underlayer to provide a patterned substrate.

Polyarylene resins of the invention may also be used in a self-aligned double patterning process. In such a process, a layer of an aromatic resin described above is coated on a substrate, such as by spin-coating. Any remaining organic solvent is removed and the polyarylene resin layer is cured to form an polyarylene resin underlayer. A suitable middle layer, such as a silicon-containing layer, is coated on the plyarylene resin underlayer. A layer of a suitable photoresist is then coated on the middle layer, such as by spin coating. The photoresist layer is then imaged (exposed) using patterned actinic radiation, and the exposed photoresist layer is then developed using the appropriate developer to provide a patterned photoresist layer. The pattern is next transferred from the photoresist layer to the middle layer and the polyarylene resin underlayer by appropriate etching techniques to expose portions of the substrate. Typically, the photoresist is also removed during such etching step. Next, a conformal silicon-containing layer is disposed over the patterned polyarylene resin underlayer and exposed portions of the substrate. Such silicon-containing layer is typically an inorganic silicon layer such as SiON or $SiO_2$ which is conventionally deposited by CVD. Such conformal coatings result in a silicon-containing layer on the exposed portions of the substrate surface as well as over the underlayer pattern, that is, such silicon-containing layer substantially covers the sides and top of the underlayer pattern. Next, the silicon-containing layer is partially etched (trimmed) to expose a top surface of the patterned polyarylene resin underlayer and a portion of the substrate. Following this partial etching step, the pattern on the substrate comprises a plurality of features, each feature comprising a line or post of the polyarylene resin underlayer with the silicon-containing layer directly adjacent to the sides of each polyarylene resin underlayer feature. Next, the polyarylene resin underlayer is removed, such as by etching, to expose the substrate surface that was under the polyarylene resin underlayer pattern, and providing a patterned silicon-containing layer on the substrate surface, where such patterned silicon-containing layer is doubled (that is, twice as many lines and/or posts) as compared to the patterned polyarylene resin underlayer.

The presence of the polar moieties on an aryl moiety of the present cyclopentadienone monomers provides improved thermal stability as compared to cyclopentadienone monomers having such polar moieties directly bonded to the cyclopentadienone ring. The presence of polar moieties, that is, solubility enhancing moieties, on an aryl moiety of the cyclopentadienone monomer greatly enhances the solubility of the present polyarylene resins as compared to conventional polyarylene resins and allows such resins to be used in a variety of electronics applications such as underlayers. The polyarylene resins of the invention are particularly useful in forming aromatic underlayers having good antireflective properties useful in the manufacture of integrated circuits.

The polyarylene resins of the invention are also useful in forming planarizing layers, gap filling layers, and protective layers in the manufacture of integrated circuits. When used as such planarizing layers, gap filling layers, or protective layers, one or more intervening material layers, such as silicon-containing layers, other aromatic resin layers, hardmask layers, and the like, are typically present between the layer of the present polyarylene resin and any photoresist layer. Typically, such planarizing layers, gap filling layers, and protective layers are ultimately patterned. A gap-filling process according to the invention comprises: (a) providing a semiconductor substrate having a relief image on a surface of the substrate, the relief image comprising a plurality of gaps to be filled; (b) applying a gap-fill composition over the relief image; and (c) heating the gap-fill composition at a temperature to cure the polyarylene resin; wherein the gap-fill composition comprises: (A) a polyarylene resin comprising as polymerized units: (i) one or more first cyclopentadienone monomers of formula (1)

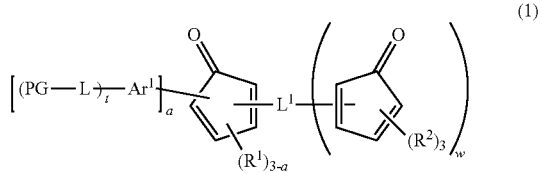

(1)

wherein each $R^1$ is independently chosen from H, $C_{1-20}$-alkyl, and optionally substituted $C_{5-30}$-aryl; each $R^2$ is independently chosen from H, $C_{1-20}$-alkyl, optionally substituted $C_{5-30}$-aryl, and (PG-L)$_t$-Ar$^1$—; PG is a polar moiety; each Ar$^1$ is independently optionally substituted $C_{5-30}$-aryl; each of L and $L^1$ is independently a linking group or a single chemical bond; L and $L^1$ may be the same as or different; a is an integer from 0 to 3; t is an integer from 1 to 4; and w is an integer from 1 to 4; provided that when a=0, $L^1$ has the formula (1a)

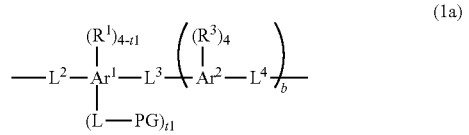

(1a)

wherein Ar$^2$ is a $C_{5-30}$-aryl; each $R^3$ is independently chosen from H, $C_{1-20}$-alkyl, optionally substituted $C_{5-30}$-aryl, and (PG-L)$_t$-Ar$^1$—; each of $L^2$, $L^3$ and $L^4$ is independently a single chemical bond or a divalent linking group; t is as described above; t1 is an integer from 1 to 4; b is 0 or 1; $L^2$, $L^3$ and $L^4$ may be the same or different; and (ii) one or more polyalkynyl-substituted second monomers; and (B) one or more organic solvents. The present compositions substantially fill, preferably fill, and more preferably fully fill, a plurality of gaps in a semiconductor substrate.

EXAMPLE 1: DIPHENYLACETONE DERIVATIVE SYNTHESIS

To a 250 mL round-bottomed flask, methyl 4-(bromomethyl)benzoate (12.10 g, 52.83 mmol), p-toluenesulfonylmethyl isocyanide (5.00 g, 25.61 mmol), and tetrabutylammonium iodide (473 mg, 1.28 mmol) were combined in 50 mL dichloromethane with magnetic stirring. The mixture was cooled to 0° C. and then a 40% w/w aqueous sodium hydroxide solution (7.16 mL) was added dropwise to the mixture with rapid stirring. The biphasic mixture was then allowed to warm to room temperature and continue to stirring rapidly for 4 hours after which the reaction was complete indicated by consumption of the methyl 4-(bromomethyl)benzoate by TLC (9:1 heptane:ethyl acetate).

Next, a separatory funnel was used to separate the two phases. The organic phase was separated and set aside and the aqueous phase was extracted twice with 20 mL portions of dichloromethane. The combined organic extracts were dried over magnesium sulfate, filtered, and concentrated in vacuo. This crude concentrated residue was dissolved in a mixture of 40 mL dichloromethane and 15 mL tetrahydrofuran. With rapid stirring, 15 mL of 6 M hydrochloric acid was added slowly dropwise and the mixture was allowed to stir at room temperature for 30 minutes. Next the reaction mixture was quenched with saturated sodium bicarbonate. A separatory funnel was used to separate the two phases. The organic phase was separated and set aside and the aqueous phase was extracted twice with 20 mL portions of dichloromethane. The combined organic extracts were dried over magnesium sulfate, filtered, and concentrated in vacuo over 10 g of silica gel. The dried solid was purified via flash column chromatography using ethyl acetate and heptane (1:20) to yield 4.51 g of Compound (8) (54% yield) confirmed by NMR, and the compound stored at or below 0° C. The overall reaction is illustrated in Reaction Scheme 2.

Reaction Scheme 2

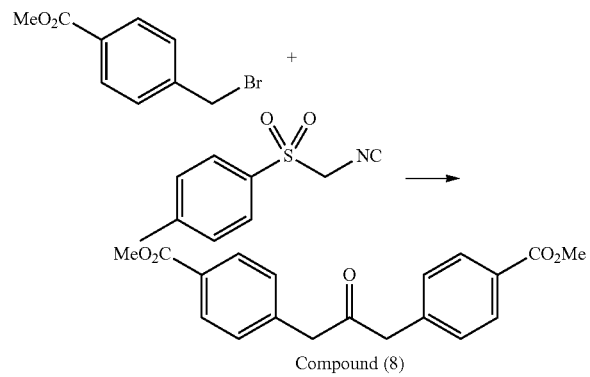

Compound (8)

EXAMPLE 2: 4,4'-OXYDIBENZIL METHYL ESTER DERIVATIVE SYNTHESIS

To a dry, nitrogen-flushed 500 mL three-neck round-bottomed flask fitted with a water-jacketed condenser and thermocouple adapter, bis(4-ethynylphenyl) ether (3.427 g, 15.70 mmol), methyl 4-bromobenzoate (8.104 g, 37.68 mmol), bis(triphenylphosphine)palladium chloride (661 mg, 0.942 mmol), copper(I) iodide (90 mg, 0.471 mmol), and anhydrous toluene (200 mL) were combined with magnetic stirring under dry nitrogen atmosphere. With stirring, triethylamine (13.13 mL, 9.533 g, 94.21 mmol) was added dropwise via syringe. The mixture was next heated to 80° C. and allowed to stir for two hours. The reaction produced a dark-red heterogeneous suspension and stirring was adjusted and increased when necessary to prevent coagulation of the suspension. The reaction was monitored via TLC for the disappearance of bis(4-ethynylphenyl) ether and observed mono-coupled intermediates. Once complete, the suspension was allowed to cool to room temperature and then vacuum filtered to isolate the solid that contained the desired product. The crude solid product was rinsed with ethyl acetate on the vacuum filter funnel to remove the excess of soluble methyl 4-bromobenzoate and until all the solid appear free of deep red coloration. Next, the solid was dried under high vacuum to yield 9.747 g of crude bis-acetylene solid (78.4% purity) before it was used directly in the next step.

To a dry, nitrogen flushed 250 mL three-neck round-bottom flask fitted with a water-jacketed condenser and thermocouple adapter, 3.00 g of the crude bis-acetylene solid from the previous step, molecular iodine (0.123 g, 0.483 mmol, 5 mol % of acetylene content), and anhydrous dimethylsulfoxide (100 mL) were added. The suspension was heated to 140° C. with stirring and maintained at that temperature for 42 hours. Next, the homogenous mixture was cooled to room temperature and then precipitated by slow dropwise addition into room temperature deionized water. The solid was isolated using vacuum filtration. The crude solid was dissolved in dichloromethane and 2.5 g of silica gel was added followed by concentration in vacuo to dryness. The silica supported crude solid was purified using flash column chromatography using a gradient from 1:1 dichloromethane/heptane to 100% dichloromethane over 15 column volumes to purify the desired product. This yielded 600 mg (22.6% yield) of Compound (9) confirmed by NMR. The overall reaction is illustrated in Reaction Scheme 3.

EXAMPLE 3

To a dry 20 mL vial equipped with a magnetic stir bar, diphenylacetone (90% purity, 80.64 mg, 0.345 mmol), Compound (9) from Example 2 (95% purity, 100 mg, 0.173 mmol), and 3 mL anhydrous ethanol were added with stirring. The capped vial containing the stirred mixture was heated to 75° C. to dissolve the starting materials. Next a solution of potassium hydroxide (29 mg) in 1 mL of ethanol was added dropwise and the vial was recapped and maintained at 75° C. for 45 minutes with stirring. Upon addition of the potassium hydroxide, the solution immediately turned dark purple. The dark color persisted through the 45 minute reaction period. After cooling to room temperature, a small amount of purple solid precipitated out of solution onto the interior surface of the vial. TLC (2:1 heptane/ethyl acetate) of the reaction mixture showed no starting reactants and a single spot on the baseline.

Next, in a 20 mL vial, a small aliquot of the reaction mixture (100 μL) diluted to 1 mL with ethanol was acidified to pH 1 using 6 M hydrochloric acid and resulted in a dramatic color change from dark purple to light red. The heterogeneous suspension of dark brown solid particles became a light red homogenous solution upon adding a few drops of the acid. This solution was next diluted with 10 mL dichloromethane and washed three times with 5 mL water (each wash), the washed organic phase was dried with magnesium sulfate, filtered, and then concentrated to dryness on a rotary evaporator. Analysis of the solid using NMR showed a mixture of products.

EXAMPLE 4

The mixture of products from Example 3 is dissolved in 1 mL of acetic anhydride and a single drop of concentrated sulfuric acid (98%) is added with stirring at room temperature. The mixture is allowed to stir at room temperature overnight. Next, the reaction mixture is added slowly, dropwise to stirred water cooled to 0° C. A solid precipitate (Compound (1b)) is expected to be isolated via vacuum filtration.

Reaction Scheme 3

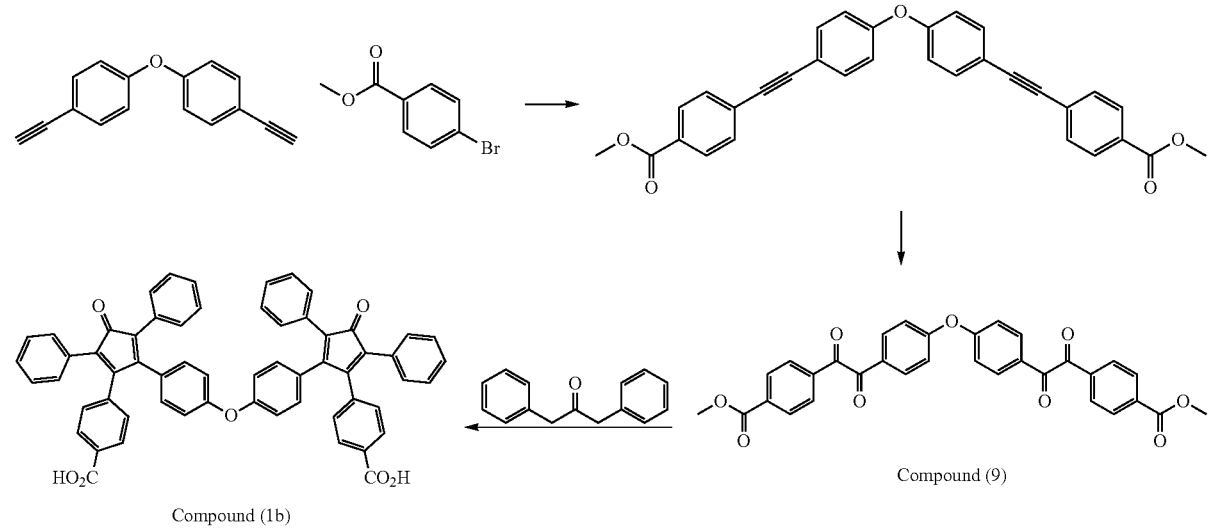

Compound (1b)

Compound (9)

EXAMPLE 5: SYNTHESIS OF COMPOUND (1H)

Phthalic anhydride (0.015 mol, 2.27 g, 1.2 eq) was charged to a dry, 250 mL, 3-neck round bottom flask. Methylene chloride (50 mL) was then charged and the solution was stirred with a magnetic stir bar under nitrogen until all of the phthalic anhydride dissolved (10 min). Next, diphenylene oxide bis(triphenylcyclopentadienone) "(DPO-CPD)" monomer (0.013 mol, 10 g, 1 eq) was charged to the round bottom flask and the solution was stirred under nitrogen until all of the solid DPO-CPD monomer was dissolved (30 min). Finally, aluminum chloride (granular, 0.066 mol, 8.855 g, 5.2 eq) was added in portions over 10 minutes. The dark black solution was then stirred at room temperature for twenty four hours. The reaction was then quenched by pouring the reaction into an HCl solution (5%, 500 mL) and stirring for twelve hours. The dark red precipitate was then filtered, collected and dried (50° C., 24 hours, reduced pressure) to afford 11.2 g (94.18%) of a dark red solid (Compound (1h)) The isolated product was soluble in PGME, and the structure was confirmed by $^1$H-NMR and gel permeation chromatography.

EXAMPLE 6: SYNTHESIS OF COMPOUND (1I)

Trimellitic anhydride chloride (0.006 mol, 1.345 g, 1 eq) was added to a dry, 250 mL, 3-neck round bottom flask. Methylene chloride (50 mL) was then charged and the solution was stirred with a magnetic stir bar under nitrogen until all of the trimellitic anhydride chloride dissolved (10 min). Next, DPO-CPD monomer (0.006 mol, 5 g, 1 eq) was charged to the round bottom flask and the solution was stirred under nitrogen until all of the solid DPO-CPD monomer was dissolved (30 min). Finally, aluminum chloride (granular, 0.042 mol, 5.535 g, 6.5 eq) was added in portions over 10 minutes. The dark black solution was then stirred at room temperature for forty eight hours. The reaction was then quenched by pouring the reaction into an HCl solution (5%, 500 mL) and stirring for twelve hours. The dark red precipitate was then filtered, collected and dried (50° C., 24 hours, reduced pressure) to afford 5.6 g (89.93%) of a dark red solid (Compound (1i)). The isolated product mixture was soluble in PGME, and the structure was confirmed by $^1$H-NMR, $^{13}$C-NMR, and gel permeation chromatography.

EXAMPLE 7: SYNTHESIS OF COMPOUND (1J)

Trimellitic anhydride chloride (0.029 mol, 6.051 g, 1.5 eq) was added to a dry, 500 mL, 3-necked round bottom flask. Methylene chloride (250 mL) was then charged and the solution was stirred with a magnetic stir bar under nitrogen until all of the trimellitic anhydride chloride dissolved (10 min). Next, DPO-CPD monomer (0.019 mol, 15 g, 1 eq) was charged to the round bottom flask and the solution was stirred under nitrogen until all of the solid DPO-CPD monomer was dissolved (30 min). Finally, aluminum chloride (granular, 0.153 mol, 20.44 g, 8 eq) was added in portions over 10 minutes. The dark black solution was then stirred at room temperature for forty eight hours. The reaction was then quenched by pouring the reaction into an HCl solution (5%, 500 mL) and stirring for twelve hours. The dark red precipitate was then filtered, collected and dried (50° C., 24 hours, reduced pressure) to afford 16.5 g (87.6%) of a dark red solid (Compound (1j)). The isolated product mixture was soluble in PGME, and the structure was confirmed by $^1$H-NMR, $^{13}$C-NMR, and gel permeation chromatography.

EXAMPLE 8

Compound (1h) from Example 5 (0.009 mol, 8.00 g, 1 eq) was first charged to a 250 mL 3-necked round bottom flask followed by the addition of 1,3,5-tris(phenylethynyl)benzene ('TRIS", 0.009 mol, 3.577 g, 1.1 eq). GBL (27.01 g) was then added and the reaction heated to 204° C. within thirty minutes. The reaction was kept at 204° C. for 10 hours and allowed to cool to room temperature. The reaction was then poured into 500 mL of DI water and stirred for one hour. The brown solid was filtered and dried (70° C., 48 hours) to afford 10.2 g of solid Polymer 1. The solid was >10% w/w soluble in PGME. Analysis of Polymer 1 by gel permeation chromatography against polystyrene standards indicated a weight average molecular weigh ($M_w$) of approximately 9000 Da.

EXAMPLE 9

Compound mixture (1j) from Example 7 (0.004 mol, 3.6 g, 1 eq) was first charged to a 100 mL 3-necked round bottom flask, followed by TRIS. (0.005 mol, 2.007 g, 1.43 eq) and GBL (13 g). The reaction was heated to 204° C. within 30 minutes and held at 204° C. for a total of 10 hours. The reaction was then allowed to cool to room temperature and poured into 250 mL of a 1% HCl solution and stirred for 12 hours. The precipitate was then filtered and dried (70° C., 48 hours) to afford 5.4 g of Polymer 2 as a brown solid. Analysis of Polymer 2 by gel permeation chromatography against polystyrene standards indicated a $M_w$ of approximately 6600 Da.

EXAMPLE 10

The solubility of Polymers 1 and 2 from Examples 8 and 9, respectively, was compared to the solubility of a conventional polyarylene resin (Comparative Polymer 1) having no polar moieties on the cyclopentadienone monomer. Comparative Polymer 1 was prepared by reacting DPO-CPD with TRIS in an approximate 1:1 ratio to yield a polymer having a Mw of approximately 8000 Da. The solubility of each polymer in PGMEA and PGME (conventional solvents used in the electronics industry) was evaluated by observing the amount of polymer to be dissolved in an amount of solvent on a w/w basis. The effect of solvent dilution on a formulation of each of the polymers (5% w/w) in PGMEA was also determined by adding each formulation separately to 10x weight equivalent of PGME ("1:10 PGME") and a 70:30 w/w mixture of PGME:PGMEA ("1:10 PP73") and determining the turbidity of the resultant dilution. Turbidity was determined using an Orbeco-Hellige Digital Direct-Reading Turbidimeter and comparing the sample solution to DI $H_2O$ as the standard "0" reading. Table 1 reports the solubility of each of the polymers in PGME and PGMEA by weight, and the relative turbidity of the diluted formulations.

TABLE 1

| Polymer | PGMEA | PGME | 1:10 PGME | 1:10 PP 73 |
| --- | --- | --- | --- | --- |
| Comparative Polymer 1 | ca. 5% | None | >200 | <10 |
| Polymer 1 | >20% | >10% | <1 | <1 |
| Polymer 2 | >20% | >10% | <1 | <1 |

The data in Table 1 clearly show that Polymers 1 and 2 show significant solubility in both PGMEA and PGME as compared to Comparative Polymer 1. A turbidity value of <1 indicates the solution is visually clear. As can be seen from the data in Table 1, dilutions of the formulations of Polymers 1 and 2 in both 10×PGME and 70:30 w/w mixture of PGME:PGMEA are visually clear, whereas the dilution of Comparative Polymer 1 shows significant turbidity.

What is claimed is:

1. A cyclopentadienone compound of formula (1)

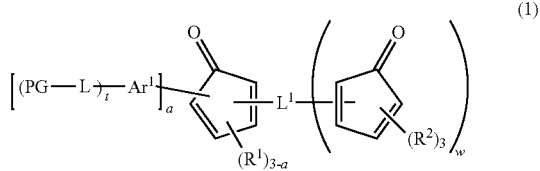

wherein each $R^1$ is independently chosen from H, $C_{1-20}$-alkyl, optionally substituted $C_{5-30}$-aryl; each $R^2$ is independently chosen from H, $C_{1-20}$-alkyl, optionally substituted $C_{5-30}$-aryl, and $(PG-L)_t$-$Ar^1$—; each PG is —C(=O)$OR^5$; $R^5$ is H; each $Ar^1$ is independently optionally substituted $C_{5-30}$-aryl; L is a single chemical bond; and $L^1$ is chosen from —O—, —$C_{1-30}$-ketoalkyl-, —$C_{1-30}$-ketoalkyl-$C_{6-30}$-aryl, —$C_6H_4$—, —$C_{10}H_6$—, —$C_6H_4$—$C_6H_4$—, —$C_6H_4$—O—$C_6H_4$—, —$C_6H_4$—O—$C_6H_4$—O—$C_6H_4$—, and groups of formula (1a); a is an integer from 0 to 3; t is an integer from 1 to 4; and w=1; provided that when a=0, $L^1$ has the formula (1a)

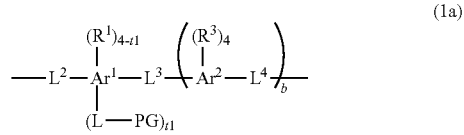

wherein $Ar^2$ is a $C_{5-30}$-aryl; each $R^3$ is independently chosen from H, $C_{1-20}$-alkyl, optionally substituted $C_{5-30}$-aryl, and $(PG-L)_t$-$Ar^1$—; each of $L^2$, $L^3$ and $L^4$ is chosen from a single chemical bond, —O—, —$C_{1-30}$-alkyl-, —$C_{1-30}$-ketoalkyl-, —$C_{1-30}$-ketoalkyl-$C_{6-30}$-aryl-, —$C_{6-30}$-aryl-, —$C_{6-30}$-aryl-O—$C_{6-30}$-aryl-, —$C_{6-30}$-aryl-O—$C_{6-30}$-aryl-O—$C_{6-30}$-aryl-, and combinations of the foregoing; t1 is an integer from 1 to 4; b is 0 or 1; and $L^2$, $L^3$ and $L^4$ may be the same or different.

2. The cyclopentadienone compound of claim 1 wherein each $Ar^1$ and $Ar^2$ is independently chosen from pyridyl, phenyl, naphthyl, acenaphthyl, fluorenyl, carbazolyl, anthracenyl, phenanthryl, pyrenyl, coronenyl, tetracenyl, pentacenyl, tetraphenyl, benzotetracenyl, triphenylenyl, perylenyl, tolyl, xylyl, dibenzothiophenyl, thioxanthonyl, indolyl, and acridinyl.

3. A polyarylene resin comprising as polymerized units one or more first cyclopentadienone monomers of claim 1, and one or more polyalkynyl-substituted second monomers.

4. The polyarylene resin of claim 3 wherein at least one polyalkynyl-substituted second monomer has the formula (2)

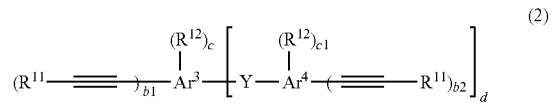

wherein each $Ar^3$ and $Ar^4$ is independently a $C_{5-30}$ aryl moiety; each $R^{11}$ is independently chosen from H, optionally substituted $C_{5-30}$-aryl, and $(PG-L^5)_{r2}$-$Ar^5$—; each $R^{12}$ is independently chosen from H, optionally substituted $C_{5-30}$ aryl, and -$L^5$-PG; PG is a polar moiety; each $Ar^5$ is independently an optionally substituted $C_{5-30}$-aryl; each $L^5$ is a single chemical bond or a divalent linking group; each Y is independently a single chemical bond or a divalent linking group chosen from —O—, —S—, —S(=O)—, —S(=O)$_2$—, —C(=O)—, —(C($R^{13}$)$_2$)$_z$—, $C_{6-30}$-aryl, and —(C($R^{13}$)$_2$)$_{z1}$—($C_{6-30}$-aryl)-(C($R^{13}$)$_2$)$_{z2}$—; each $R^{13}$ is independently chosen from H, hydroxy, halo, $C_{1-10}$-alkyl, $C_{1-10}$-haloalkyl, and optionally substituted $C_{6-30}$-aryl; t2=1 to 4; b1=1 to 4; each b2=0 to 2; b1+ each b2=2 to 6; c=0 to 4; each c1=3 to 5; d=0 to 2; z=1 to 10; b1+c+d=6; z1=0 to 10; z2=0 to 10; and z1+z2=1 to 10.

5. The polyarylene resin of claim 4 wherein b1=2 or 3 and d=0.

6. The polyarylene resin of claim 4 wherein $R^{12}$ is H, or $C_{6-10}$-aryl.

7. A polyarylene resin composition comprising the polyarylene resin of claim 3 and one or more organic solvents.

8. A method of manufacturing an electronic device comprising providing a substrate; coating a layer of the polyarylene resin composition of claim 7 on a surface of the substrate; removing any organic solvent; and curing the polyarylene resin to form a dielectric material layer.

9. A method of forming a patterned layer comprising: (a) coating on a substrate a layer of a polyarylene resin composition of claim 7; (b) removing organic solvent to form a polyarylene resin layer; (c) coating a layer of a photoresist on the polyarylene resin layer; (d) exposing the photoresist layer to actinic radiation through a mask; (e) developing the exposed photoresist layer to form a resist pattern; and (f) transferring the pattern to the polyarylene resin layer to expose portions of the substrate.

10. The method of claim 9 wherein at least one polyalkynyl-substituted second monomer has the formula (2)

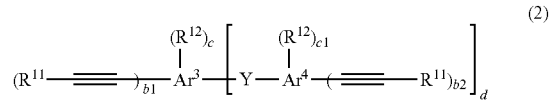

wherein each $Ar^3$ and $Ar^4$ is independently a $C_{5-30}$ aryl moiety; each $R^{11}$ is independently chosen from H, optionally substituted $C_{5-30}$-aryl, and $(PG-L^5)_{r2}$-$Ar^5$—; each $R^2$ is independently chosen from H, optionally substituted $C_{5-30}$ aryl, and -$L^5$-PG; PG is a polar moiety; each $Ar^5$ is independently an optionally substituted $C_{5-30}$-aryl; each $L^5$ is a single chemical bond or a divalent linking group; each Y is independently a single chemical bond or a divalent linking group chosen from —O—, —S—, —S(=O)—, —S(=O)$_2$—, —C(=O)—, —(C($R^{13}$)$_2$)$_z$—, $C_{6-30}$-aryl, and —(C($R^{13}$)$_2$)$_{z1}$—($C_{6-30}$-aryl)-(C($R^{13}$)$_2$)$_{z2}$—; each $R^{13}$ is independently chosen from H, hydroxy, halo, $C_{1-10}$- alkyl, $C_{1-10}$-haloalkyl, and optionally substituted $C_{6-30}$-aryl; t2=1 to 4; b1=1 to 4; each b2=0 to 2; b1+ each b2=2 to 6; c=0 to 4; each c1=3 to 5; d=0 to 2; z=1 to 10; b1+c+d=6; z1=0 to 10; z2=0 to 10; and z1+z2=1 to 10.

\* \* \* \* \*